(12) United States Patent
Kermani et al.

(10) Patent No.: US 7,499,806 B2
(45) Date of Patent: Mar. 3, 2009

(54) IMAGE PROCESSING IN MICROSPHERE ARRAYS

(75) Inventors: Bahram Ghaffarzadeh Kermani, San Diego, CA (US); Juergen Haas, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

(21) Appl. No.: 10/504,568

(22) PCT Filed: Feb. 14, 2003
(Under 37 CFR 1.47)

(86) PCT No.: PCT/US03/04570

§ 371 (c)(1),
(2), (4) Date: May 6, 2005

(87) PCT Pub. No.: WO03/069333

PCT Pub. Date: Aug. 21, 2003

(65) Prior Publication Data

US 2006/0041384 A1   Feb. 23, 2006

Related U.S. Application Data

(60) Provisional application No. 60/357,213, filed on Feb. 14, 2002.

(51) Int. Cl.
*G06F 17/11* (2006.01)
*G06F 17/50* (2006.01)
*C12Q 1/68* (2006.01)
*C12M 1/00* (2006.01)

(52) U.S. Cl. .............................. 702/19; 702/28; 702/32; 382/132; 435/6; 435/71; 435/174; 435/283.1; 435/287.2

(58) Field of Classification Search .................... 702/28, 702/32; 382/132
See application file for complete search history.

(56) References Cited

U.S. PATENT DOCUMENTS

| | | |
|---|---|---|
| 4,200,110 A | 4/1980 | Peterson et al. |
| 4,469,863 A | 9/1984 | Ts'o |
| 4,499,052 A | 2/1985 | Fulwyler |
| 4,682,895 A | 7/1987 | Costello |
| 4,785,814 A | 11/1988 | Kane |
| 4,822,746 A | 4/1989 | Walt |
| 4,824,789 A | 4/1989 | Yafuso et al. |
| 4,981,783 A | 1/1991 | Augenlicht |
| 4,991,579 A | 2/1991 | Allen |
| 4,999,306 A | 3/1991 | Yafuso et al. |
| 5,002,867 A | 3/1991 | Macevicz |
| 5,028,545 A | 7/1991 | Soini |
| 5,034,506 A | 7/1991 | Summerton et al. |
| 5,105,305 A | 4/1992 | Betzig et al. |
| 5,114,864 A | 5/1992 | Walt |
| 5,129,015 A | 7/1992 | Allen et al. |
| 5,129,155 A | 7/1992 | Hoffman et al. |
| 5,132,242 A | 7/1992 | Cheung |
| 5,143,853 A | 9/1992 | Walt |
| 5,194,300 A | 3/1993 | Cheung |
| 5,216,141 A | 6/1993 | Benner |
| 5,235,033 A | 8/1993 | Summerton et al. |
| 5,244,636 A | 9/1993 | Walt et al. |
| 5,244,813 A | 9/1993 | Walt et al. |
| 5,245,676 A | 9/1993 | Spitz |
| 5,250,264 A | 10/1993 | Walt et al. |
| 5,252,494 A | 10/1993 | Walt |
| 5,254,477 A | 10/1993 | Walt et al. |
| 5,270,163 A | 12/1993 | Gold et al. |
| 5,298,741 A | 3/1994 | Walt et al. |
| 5,302,509 A | 4/1994 | Cheeseman |
| 5,320,814 A | 6/1994 | Walt et al. |
| 5,357,590 A | 10/1994 | Auracher |
| 5,380,489 A | 1/1995 | Sutton et al. |
| 5,386,023 A | 1/1995 | Sanghvi et al. |
| 5,435,724 A | 7/1995 | Goodman et al. |
| 5,474,895 A | 12/1995 | Ishii et al. |
| 5,475,096 A | 12/1995 | Gold et al. |
| 5,481,629 A | 1/1996 | Tabuchi |
| 5,494,798 A | 2/1996 | Gerdt et al. |
| 5,494,810 A | 2/1996 | Barany et al. |

(Continued)

FOREIGN PATENT DOCUMENTS

EP    0269764    6/1988

(Continued)

OTHER PUBLICATIONS

Seitz, W.R., "Chemical Sensors Based on Immobilized Indicators and Fiber Optics." *CRC Critical Review in Analytical Chemistry* 1988, vol. 19, pp. 135-173.

(Continued)

*Primary Examiner*—Michael Borin
(74) *Attorney, Agent, or Firm*—Knobbe Martens Olson & Bear LLP

(57) ABSTRACT

Described herein are methods for registering analytical images comprising obtaining an image of an array, wherein the image depicts fiducials that can be used to register the sequential images of the array by determining the average intensity of the fiducials and then positioning the sequential images such that the average intensity of the fiducials attains either a maximum or minimum value.

11 Claims, 12 Drawing Sheets

U.S. PATENT DOCUMENTS

| | | | |
|---|---|---|---|
| 5,496,997 | A | 3/1996 | Pope |
| 5,512,490 | A | 4/1996 | Walt et al. |
| 5,516,635 | A | 5/1996 | Ekins et al. |
| 5,565,324 | A | 10/1996 | Still et al. |
| 5,567,588 | A | 10/1996 | Gold et al. |
| 5,573,909 | A | 11/1996 | Singer et al. |
| 5,575,849 | A | 11/1996 | Honda et al. |
| 5,595,877 | A | 1/1997 | Gold et al. |
| 5,602,240 | A | 2/1997 | Mesmaeker et al. |
| 5,633,972 | A | 5/1997 | Walt et al. |
| 5,637,459 | A | 6/1997 | Burke et al. |
| 5,637,684 | A | 6/1997 | Cook et al. |
| 5,639,603 | A | 6/1997 | Dower et al. |
| 5,644,048 | A | 7/1997 | Yau |
| 5,656,241 | A | 8/1997 | Seifert et al. |
| 5,679,524 | A | 10/1997 | Nikiforov et al. |
| 5,683,867 | A | 11/1997 | Biesecker et al. |
| 5,690,894 | A | 11/1997 | Pinkel et al. |
| 5,705,337 | A | 1/1998 | Gold et al. |
| 5,795,716 | A | 8/1998 | Chee et al. |
| 5,814,524 | A | 9/1998 | Walt |
| 5,830,711 | A | 11/1998 | Barany et al. |
| 5,840,256 | A | 11/1998 | Demers et al. |
| 5,854,684 | A | 12/1998 | Stabile et al. |
| 5,856,083 | A | 1/1999 | Chelsky et al. |
| 5,858,732 | A | 1/1999 | Solomon et al. |
| 5,863,708 | A | 1/1999 | Zanzucchi et al. |
| 5,888,723 | A | 3/1999 | Sutton et al. |
| 5,900,481 | A | 5/1999 | Lough et al. |
| 6,013,456 | A | 1/2000 | Akhavan-Tafti |
| 6,023,540 | A | 2/2000 | Walt et al. |
| 6,027,889 | A | 2/2000 | Barany et al. |
| 6,040,138 | A | 3/2000 | Lockhart et al. |
| 6,051,380 | A | 4/2000 | Sosnowski et al. |
| 6,054,564 | A | 4/2000 | Barany et al. |
| 6,060,288 | A | 5/2000 | Adams et al. |
| 6,078,390 | A | 6/2000 | Bengtsson |
| 6,083,763 | A | 7/2000 | Balch |
| 6,090,555 | A | 7/2000 | Fiekowsky et al. |
| 6,110,678 | A | 8/2000 | Weisburg et al. |
| 6,172,218 | B1 | 1/2001 | Brenner |
| 6,200,737 | B1 | 3/2001 | Walt et al. |
| 6,210,910 | B1 | 4/2001 | Walt et al. |
| 6,228,575 | B1 | 5/2001 | Gingeras et al. |
| 6,245,517 | B1 | 6/2001 | Chen et al. |
| 6,251,639 | B1 | 6/2001 | Kurn |
| 6,268,148 | B1 | 7/2001 | Barany et al. |
| 6,296,702 | B1 | 10/2001 | Bryning et al. |
| 6,327,410 | B1 * | 12/2001 | Walt et al. ............ 385/115 |
| 6,406,845 | B1 | 6/2002 | Walt et al. |
| 2002/0132221 | A1 | 9/2002 | Chee et al. |
| 2002/0150909 | A1 | 10/2002 | Stuelpnagel et al. |

FOREIGN PATENT DOCUMENTS

| | | |
|---|---|---|
| EP | 0392546 | 10/1990 |
| EP | 0478319 | 4/1992 |
| EP | 0723146 | 7/1996 |
| WO | WO89/11101 | 11/1989 |
| WO | WO93/02360 | 2/1993 |
| WO | WO93/25563 | 12/1993 |
| WO | WO96/03212 | 2/1996 |
| WO | WO97/14028 | 4/1997 |
| WO | WO97/14928 | 4/1997 |
| WO | WO97/31256 | 8/1997 |
| WO | WO97/40385 | 10/1997 |
| WO | WO98/05025 | 2/1998 |
| WO | WO98/09163 | 3/1998 |
| WO | WO98/13523 | 4/1998 |
| WO | WO98/21193 | 5/1998 |
| WO | WO98/40726 | 9/1998 |
| WO | WO98/50782 | 11/1998 |
| WO | WO98/53093 | 11/1998 |
| WO | WO98/53300 | 11/1998 |
| WO | WO99/14387 | 3/1999 |
| WO | WO99/18434 | 4/1999 |
| WO | WO99/60170 | 11/1999 |
| WO | WO99/67414 | 12/1999 |
| WO | WO99/67641 | 12/1999 |
| WO | WO00/04372 | 1/2000 |
| WO | WO00/09183 | 2/2000 |
| WO | WO00/13004 | 3/2000 |
| WO | WO00/16101 | 3/2000 |
| WO | WO00/39587 | 7/2000 |
| WO | WO00/47996 | 8/2000 |
| WO | WO00/48000 | 8/2000 |
| WO | WO00/58516 | 10/2000 |
| WO | WO00/63437 | 10/2000 |
| WO | WO00/71243 | 11/2000 |
| WO | WO00/71992 | 11/2000 |
| WO | WO00/71995 | 11/2000 |
| WO | WO00/75373 | 12/2000 |

OTHER PUBLICATIONS

Angel, S.M., "Optrodes: Chemically Selective Fiber-Optic Sensors." *Spectroscopy* 1987, vol. 2, No. 4, pp. 38-46.

Freeman, et al., "Oxygen Probe Based on Tetrakis(alkylamino)ethylene Chemiluminescence." *Anal. Chem.* 1981, vol. 53, pp. 98-102.

Lippitsch, et al., "Fibre-Optic Oxygen Sensor with the Fluorescence Decay Time as the Information Carrier." *Analytica Chimica Acta*, 1988, vol. 205, pp. 1-6.

Wolfbeis, et al., "Fiber-Optic Florosensor for Oxygen and Carbon Dioxide." *Anal. Chem.* 1988, vol. 60, pp. 2028-2030.

Jordan, et al., "Physiological pH Fiber-Optic Chemical Sensor Based on Energy Transfer." *Anal. Chem.* 1987, vol. 59, pp. 437-439.

Munkholm, et al., "A Fiber-Optic Sensor For $CO_2$ Measurement." *Talanta* 1988, vol. 35, No. 2, pp. 109-112 (Pergamon Journals, Ltd, Great Britain).

Munkholm, et al., "Polymer Modification of Fiber Optic Chemical Sensors as a Method of Enhancing Fluorescence Signal for pH Measurement." *Anal. Chem.* 1986, vol. 58, pp. 1427-1430.

Seitz, W. R., "Chemical Sensors Based on Fiber Optics." *Anal. Chem.* 1984, vol. 56, No. 1, pp. 16A-34A.

Peterson, et al., "Fiber Optic pH Probe for Physiological Use." *Anal. Chem.* 1980, vol. 52, pp. 864-869.

Saari, et al., "pH Sensor Based on Immobilized Fluoresceinamine." *Anal. Chem.* 1982, vol. 54, pp. 821-823.

Saari, et al., "Immobilized Morin as Fluorescence Sensor for Determination of Aluminum (III)." *Anal. Chem.* 1983, vol. 55, pp. 667-670.

Zhujun, et al., "A Fluorescence Sensor for Quantifying pH in the Range From 6.5 to 8.5." *Analytica Chimica Acta*, 1984, vol. 160, pp. 47-55.

Schwab, et al., "Versatile, Efficient Raman Sampling with Fiber Optics." *Anal. Chem.* 1984, vol. 56, pp. 2199-2204.

Pantano, et al., "Analytical Applications of Optical Imaging Fibers." *Anal. Chem.* 1995, vol. 67, pp. 481A-487A.

Beaucage, et al., "The Functionalization of Oligonucleotides Via Phosphoramidite Derivatives." *Tetrahedron* 1993, vol. 49, No. 10, pp. 1925-1963. (Pergamon Journals, Ltd, Great Britain).

Lestinger, et al., "Phosphoramidate Analogs of Oligonucleotides." *J. Org. Chem.*, 1970, vol. 35, No. 11, pp. 3800-3803.

Sprinzl, et al., "Enzymatic Incorporation of ATP and CTP Analogues into the 3' End tRNA." *Eur. J. Biochem.* vol. 81, 1977, pp. 579-589.

Sawai, "Synthesis and Properties of Oligoadenylic Acids Containing 2'-5' Phosphoramide Linkage." *Chemistry Letters* 1984, pp. 805-808.

Lestinger, et al., "Effects of Pendant Groups at Phosphorus on Binding Properties of d-ApA Analogues" *Nucl. Acids Res.* 1986, vol. 14, No. 8, pp. 3487-3499.

Lestinger, et al., "Cationic Oligonucleotides." *J. Am. Chem. Soc.* 1988, vol. 110, pp. 4470-4471.

Pauwels, et al., "Biological Activity of New 2-5A Analogues." *Chemica Scripta* 1986, vol. 26, pp. 141-145.

Mag, et al., "Synthesis and Selective Cleavage of an Oligodeoxynucleotide Containing a Bridged Internucleotide 5'-phsphorothioate Linkage." *Nucleic Acids Res.* 1991, vol. 19, No. 7, pp. 1437-1441.

Brill, et al., "Synthesis of Oligodeoxynucleoside Phosphorodithioates via Thioamidites." *J. Am. Chem. Soc.* 1989, vol. 111, pp. 2321-2322.

Egholm, et al., "Peptide Nucleic Acids (PNA). Oligonucleotide Analogues with an Achiral Peptide Backbone." *J. Am. Chem. Soc.* 1992, vol. 114, pp. 1895-1897.

Meier, et al., "Peptide Nucleic Acids (PNAs)—Unusual Properties of Nonionic Oligonucleotide Analogues." *Angew. Chem. Int. Ed. Engl.* 1992, vol. 31, No. 8, pp. 10081010.

Egholm, et al., "PNA Hybridizes to Complementary Oligonucleotides Obeying the Watson-Crick Hydrogen-bonding Rules." *Nature* 1993, vol. 365, pp. 566-568.

Carlsson, et al., "Screening for Genetic Mutation." *Nature* 1996, vol. 380, p. 207.

Dempcy, et al., "Synthesis of a Thymidyl Pentamer of Deoxyribonucleic Guanidine and Binding Studies with DNA Homopolynucleotides." *Proc. Natl. Acad. Sci.* 1995, vol. 92, pp. 6097-6101.

Kiedrowski, et al., "Parabolic Growth of a Self-Replicating Hexadeoxynucleotide Bearing a 3'-5'-Phosphoamidate Linkage." *Angew. Chem. Intl. Ed. Engl.* 1991, vol. 30, No. 4, pp. 423-426.

Jung, et al., "Hybridization of Alternating Cationic/Anionic Oligonucleotides to RNA Segments." *Nucleosides and Nucleotides* 1994, vol. 13, Nos. 6 & 7, pp. 1597-1605.

Mesmaeker, A.D. et al., "Novel Backbone Replacements for Oligonucleotides." Sanghvi, Y.S. and Cook, P.D. ;Eds. *ACS Symposium Series 580—Carbohydrate Modifications in Antisense Research*, American Chemical Society, Washington DC, 1994, Chpt. 2, pp. 24-39.

Maddry, J. A., et al., "Synthesis of Nonionic Oligonucleotide Analogues." Sanghvi, Y.S. and Cook, P.D. ;Eds. *ACS Symposium Series 580—Carbohydrate Modifications in Antisense Research*, American Chemical Society, Washington DC, 1994, Chpt. 3, pp. 40-51.

Herdewijn, P., et al., "Hexopyranosyl-Like Oligonucleotides." Sanghvi, Y.S. and Cook, P.D. ;Eds. *ACS Symposium Series 580—Carbohydrate Modifications in Antisense Research*, American Chemical Society, Washington DC, 1994, Chpt. 6, pp. 80-99.

Bolli, M., et al., "α-Bicyclo-DNA: Synthesis, Characterization, and Pairing Properties of α-DNA-Analogues with Restricted Conformational Flexibility in the Sugar-Phosphate Backbone." Sanghvi, Y.S. and Cook, P.D. ;Eds. *ACS Symposium Series 580—Carbohydrate Modifications in Antisense Research*, American Chemical Society, Washington DC, 1994, Chpt. 7, pp. 100-117.

Mesmaeker, A.D., et al., "Comparison of Rigid and Flexible Backbones in Antisense Oligonucleotides." *Bioorganic and Medicinal Chem. Lett.* 1994, vol. 4, No. 3, pp. 395-398.

Gao, X., et al., "Unusual Conformation of a 3'-thioformacetal Linkage in a DNA Duplex." *J. Biomolecular NMR* 1994, vol. 4, pp. 17-34.

Horn, T., et al., "Oligonucleotides with Alternating Anionic and Cationic Phosphoramidate Linkages: Synthesis and Hybridization of Stereo-uniform Isomers." *Tetrahedron Lett.* 1996, vol. 37, No. 6, pp. 743-746. (Pergamon Journals, Ltd, Great Britain).

Jenkins, G. N., et al., "The Biosynthesis of Carbocyclic Nucleosides." *Chem. Soc. Rev.* 1995, pp. 169-176.

Rawls, R.L., "Optimistic About Antisense—Promising Clinical Results and Chemical Strategies for Further Improvements Delight Antisense Drug Researchers." *C & E News* Jun. 2, 1997, pp. 35-39.

Torchilin, et al., "The Antibody-Linked Chelating Polymers for Nuclear Therapy and Diagnostics." *Critical Rev. Therapeutic Drug Carrier Systems* 1991, vol. 7, Issue 4, pp. 275-308.

Slinkin, et al., "Terminal-Modified Polylysine-Based Chelating Polymers: Highly Efficient Coupling to Antibody with Minimal Loss in Immunoreactivity." *Bioconj. Chem.* 1991, vol. 2, pp. 342-348.

Trubetskoy, et al., "Use of N-Terminal Modified Poly(L-lysine)-Antibody Conjugate as a Carrier for Targeted Gene Delivery in Mouse Lung Endothelial Cells." *Bioconj. Chem.* 1992, vol. 3, pp. 323-327.

King, et al., "Improved Tumor Targeting with Chemically Cross-Linked Recombinant Antibody Fragments." *Cancer Res.* vol. 1994, vol. 54, pp. 6176-6185.

Wilbur, et al., "Monoclonal Antibody Fab' Fragment Cross-Linking Using Equilibrium Transfer Alkylation Reagents. A Strategy for Site-Specific Conjugation of Diagnostic and Therapeutic Agents with $F(ab')_2$ Fragments." *Bioconjugate Chem.* 1994, vol. 5, pp. 220-235.

Wang, et al., "Large-Scale Identification, mapping, and Genotyping of Single-Nucleotide Polymorphisms in the Human Genome." *Science* May 15, 1998, vol. 280, pp. 1077-1082.

Schafer, et al., "DNA variation and the Future of Human Genetics." *Nature Biotechnology* Jan. 1998, vol. 16, pp. 3-39.

Abel (1996). Analytical Chemistry 68:2905-2912.

Anonymous (Feb. 1997). Fluorescent Microspheres. Tech Note 19. Bangs Laboratories.

Anonymous (Aug. 1997). Microsphere detection guide. Bangs Laboratories.

Bangs, L. B. (Apr. 1996. The Latex Course. Bangs Laboratories.

Barnard. (1991). Nature 353:338-340.

Chen (2000). Genome Research 10: 549-557.

Czarnik (1998). Modern Drug Discovery 1.

Drmanac et al. (1990). Scientia Yugoslavica 16.

Drmanac (1994). Automated DNA Sequencing and Analysis.

Drmanac et al. (1992). Inter. J. of Genome Research 1.

Drmanac et al. (1990). The First International Conf. of Electrophoresis, Florida State University, 10-13.

Ferguson, J. A. (1996). Nature Biotechnology 14.

Fuh (1987). Analyst 112: 1159-1163.

Healey (1995). SPIE Proc. 2388: 568-573.

Healey, B. G. et al. (1997). Analytical Biochemistry 251: 270-279.

Healey (1995). Analytical Chemistry 67: 4471-4476.

Hirchfeld (1987). J. Lightwave Technology LT-5: 1027-1033.

Iannone (2000). Cytometry 39: 131-140.

Lyamichev (1999). Nature Biotechnology 17: 292-296.

Michael (1997). Proc. 3rd. Intl. Symp. Microstructures and Microfabricated Systems, 152-157.

Michael (1998). Proc. SPIE 3270: 34-41.

Michael (1998). Analytical Chemistry 70: 1242-1248.

Mignani (1995). J. Lightwave Technology 31: 1396-1406.

Pantano (1996). Chem. Mater 8: 2832-2835.

Peterson, et al. (1980). Analytical Chemistry 67: 2635-2643.

Peterson, et al. (1984). Science 13: 123-127.

Piunno (1995). Analytical Chemistry 67: 2635-2643.

Pope (1995) SPIE 2388: 245-256.

Shoemaker (1996). Nature Genetics 14: 450-456.

Strachan (1995). Letters in Applied Microbiology 21: 5-9.

Walt (1998). Accounts of Chemical Reseach 31: 267-278.

Walt (1992). Proc. IEEE 80: 903-911.

\* cited by examiner

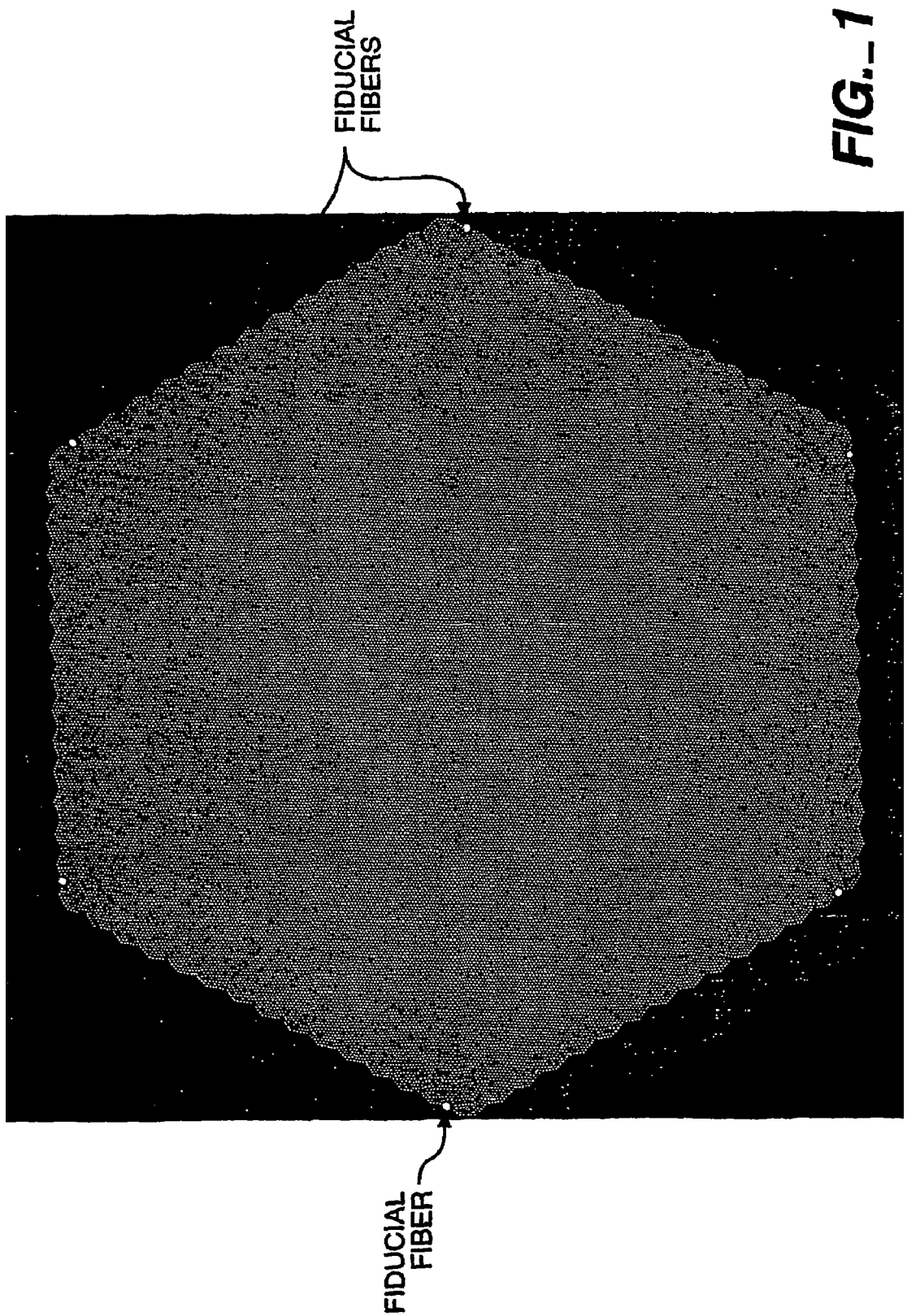
FIG._1

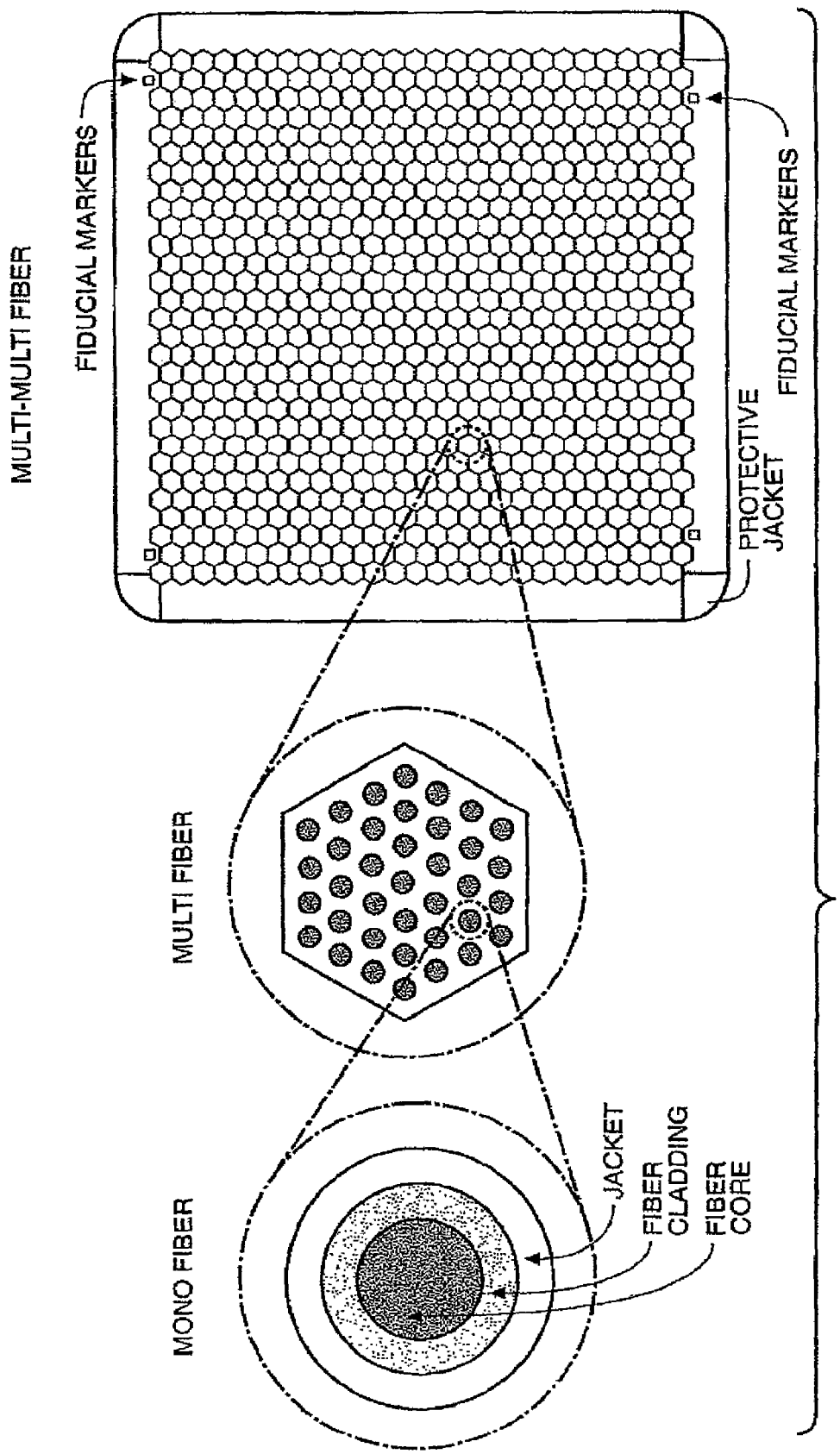
FIG._2

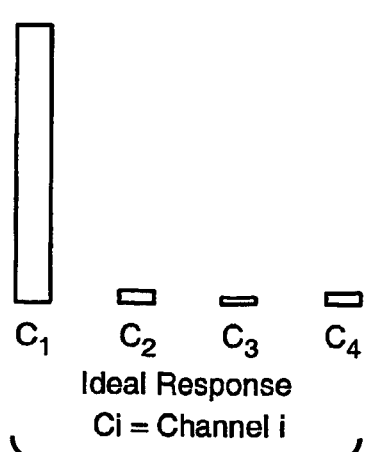
FIG._3A
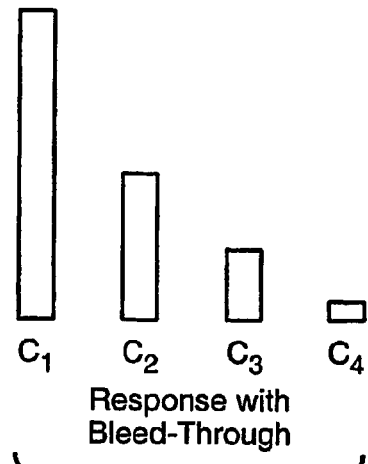
FIG._3B
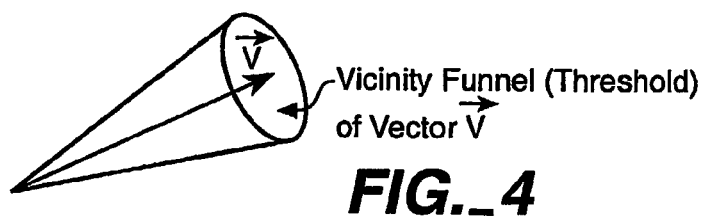
FIG._4
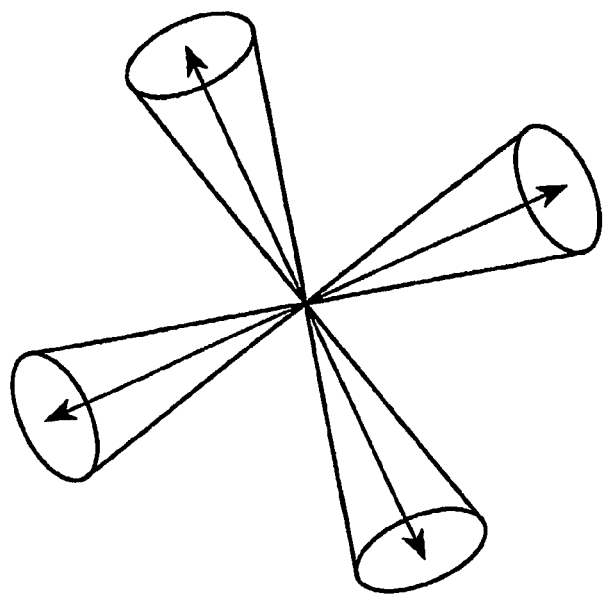
FIG._5

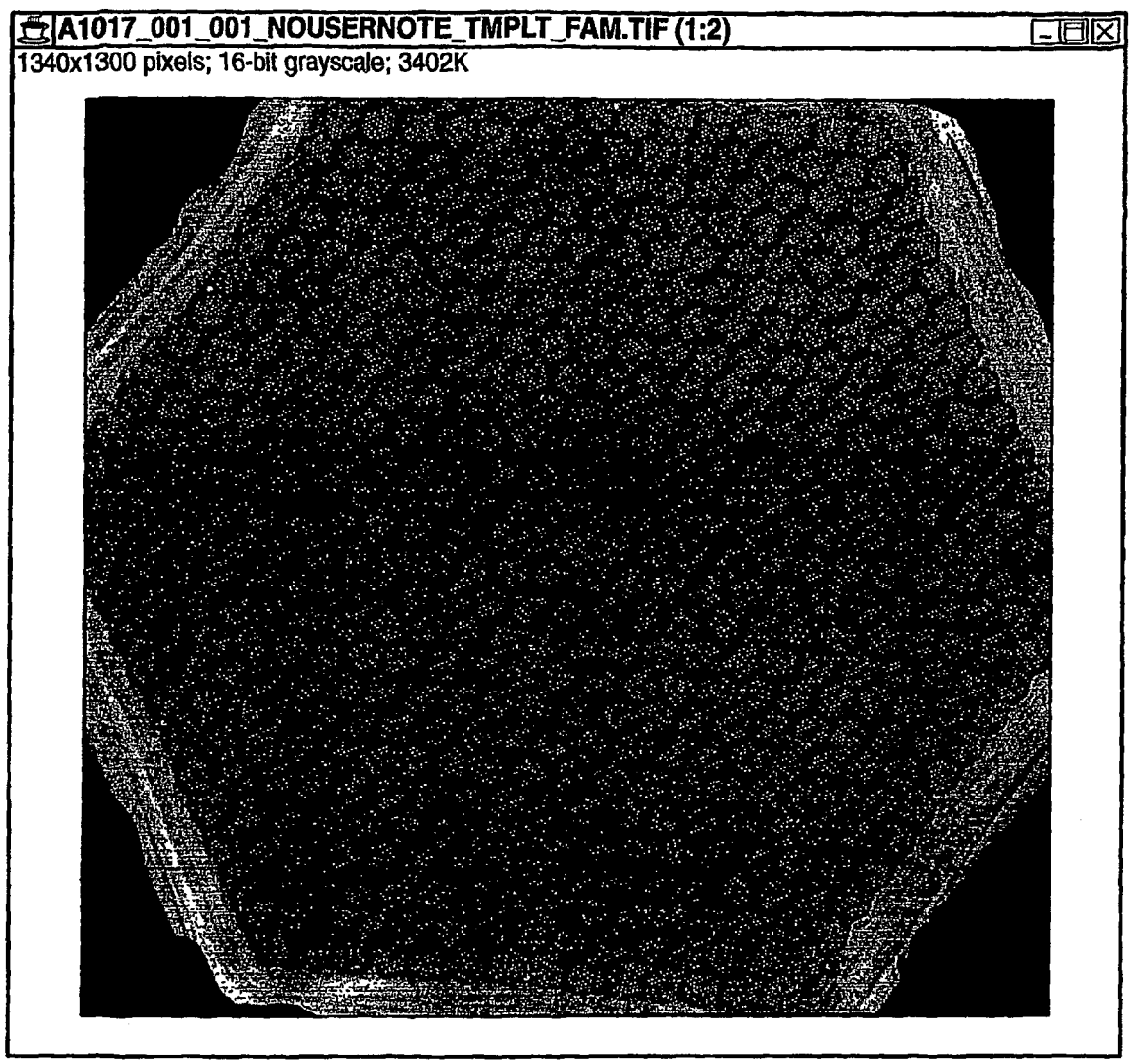
Fit Cluster of Minibundle Grids to Determine Orientation, Scale, and Phase
FIG._6A

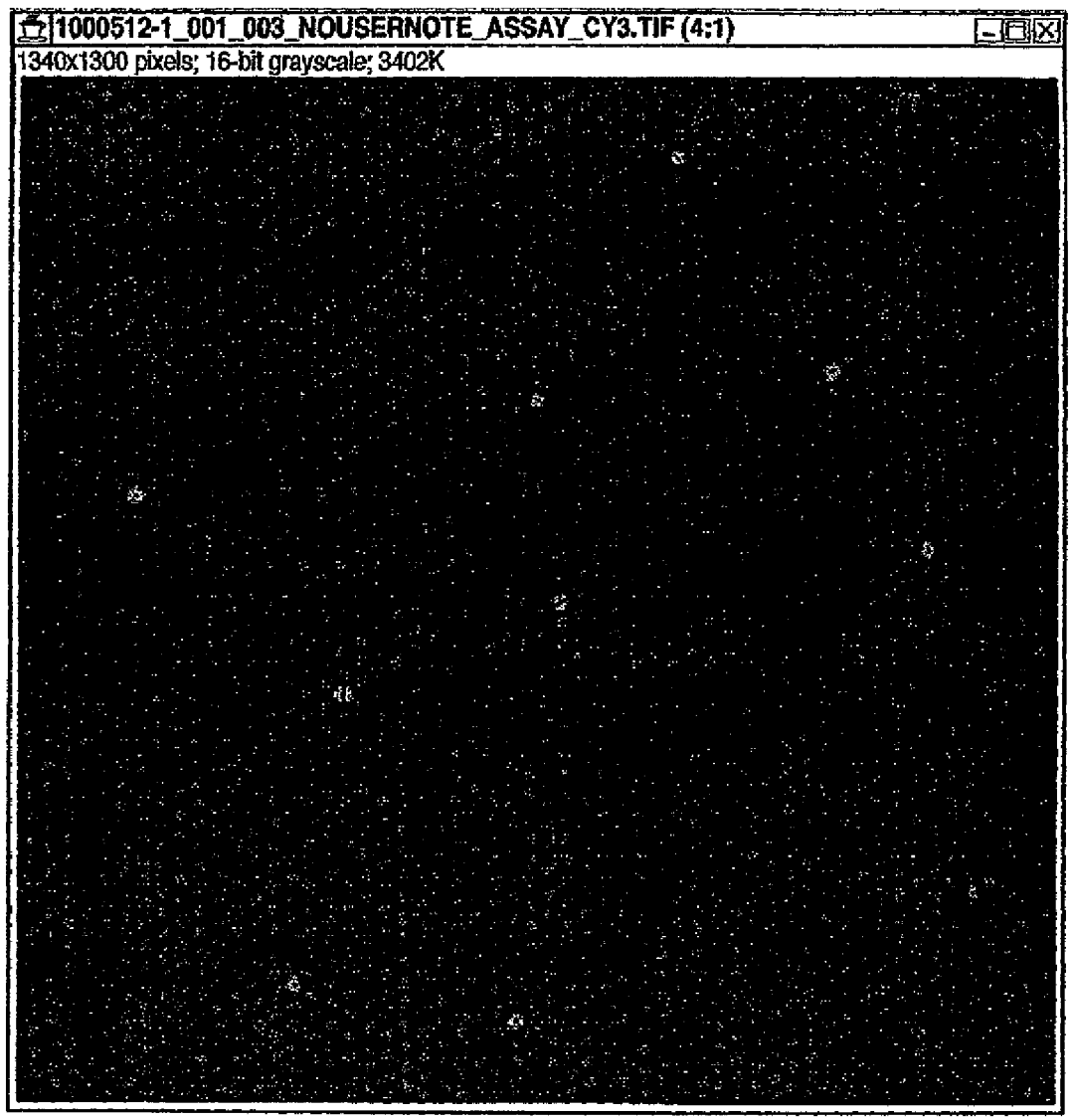
Analytical Image Registered Without Template or Decoding Info - Enlarged View
*FIG._6B*

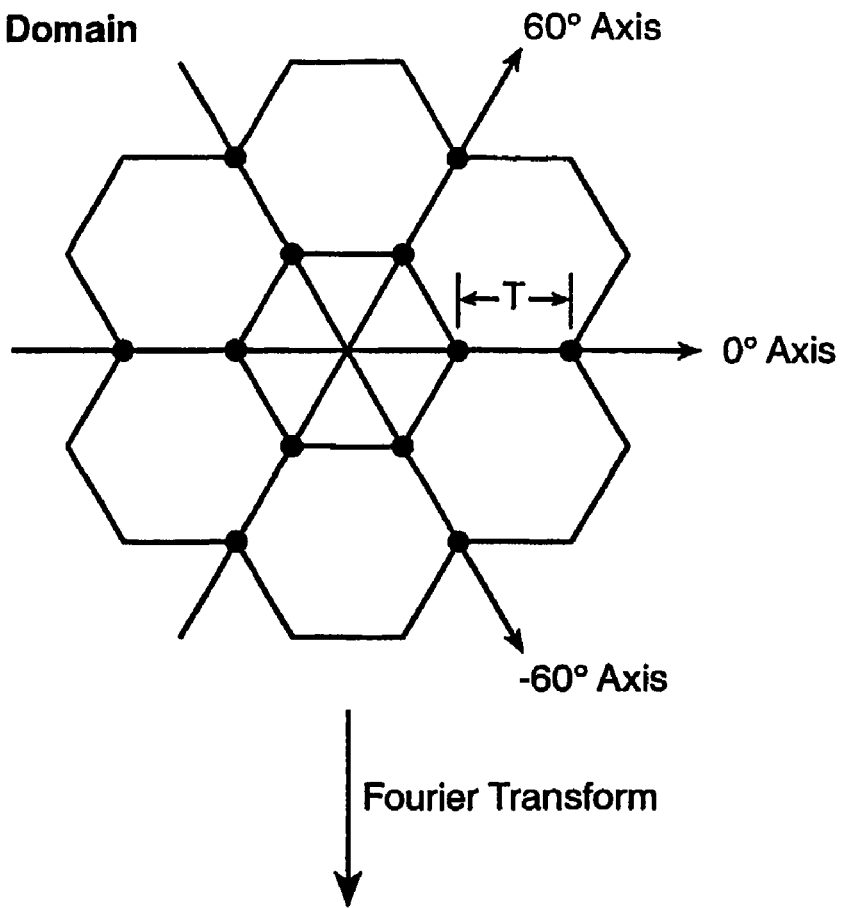
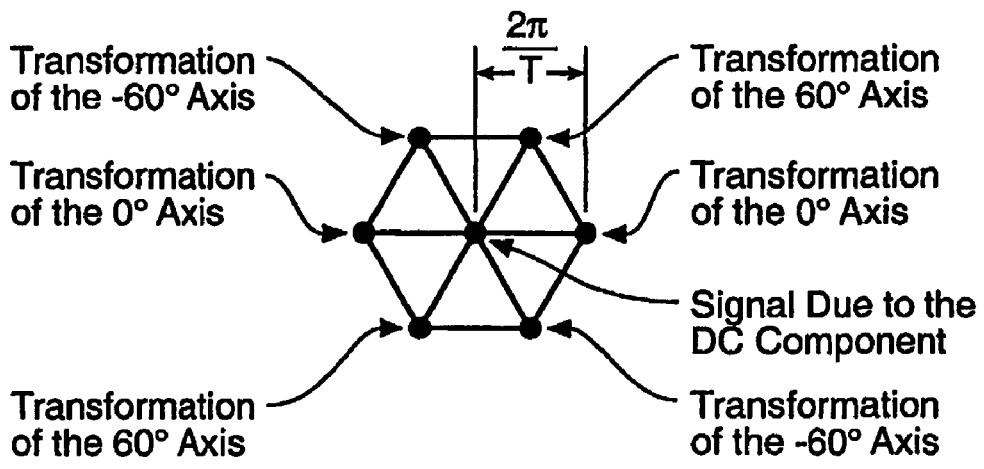
FIG._7

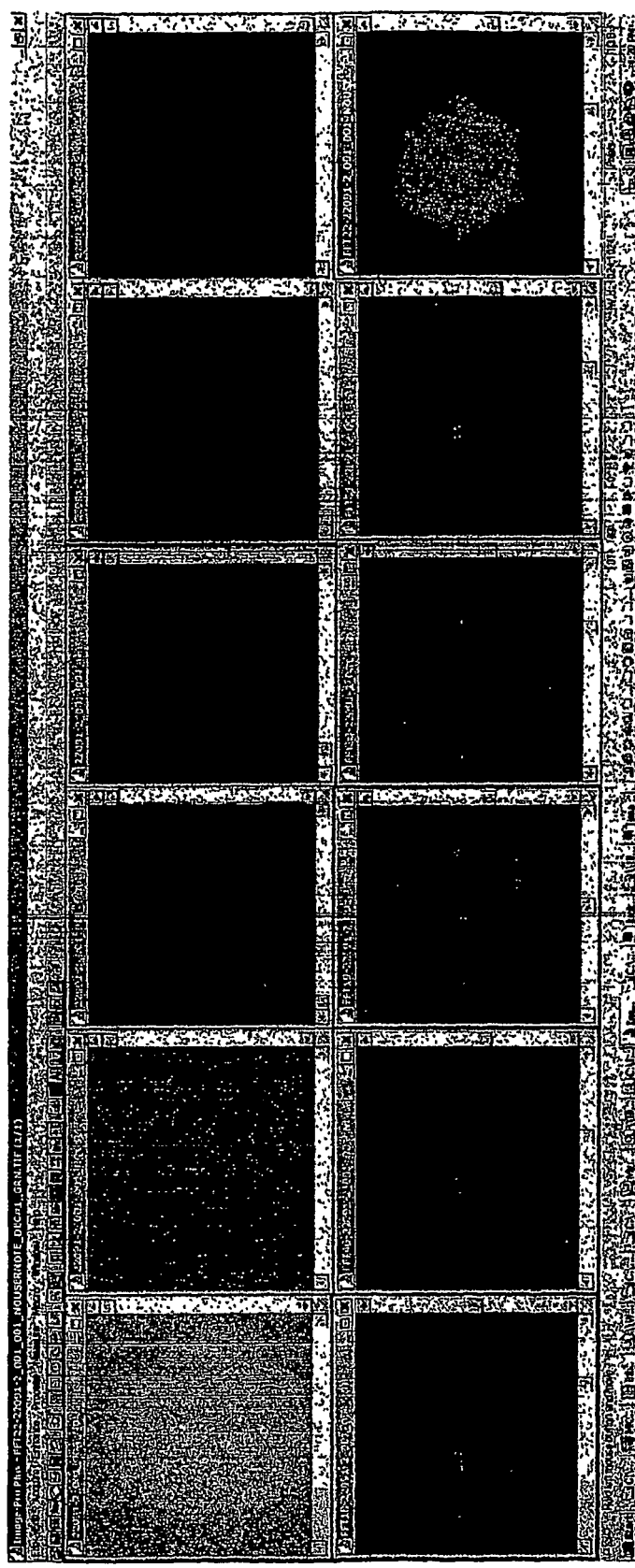
FIG._8A

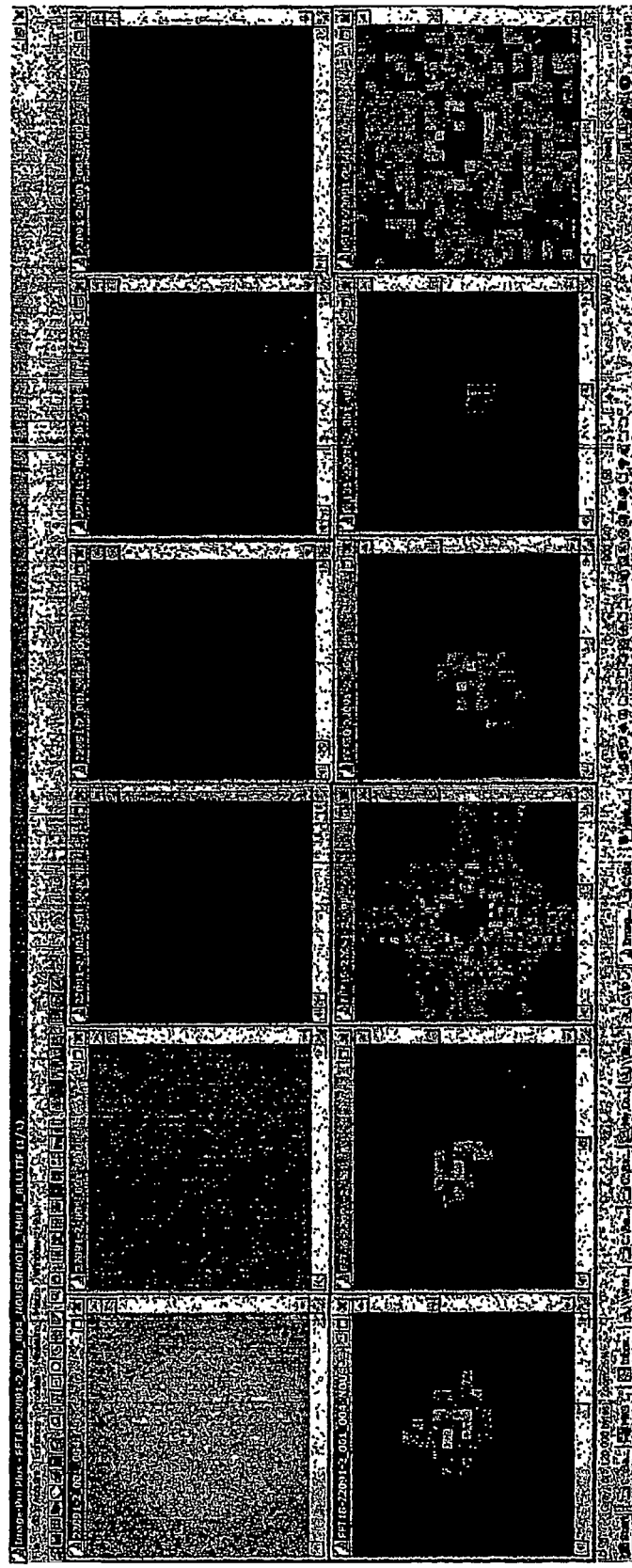
FIG._8B

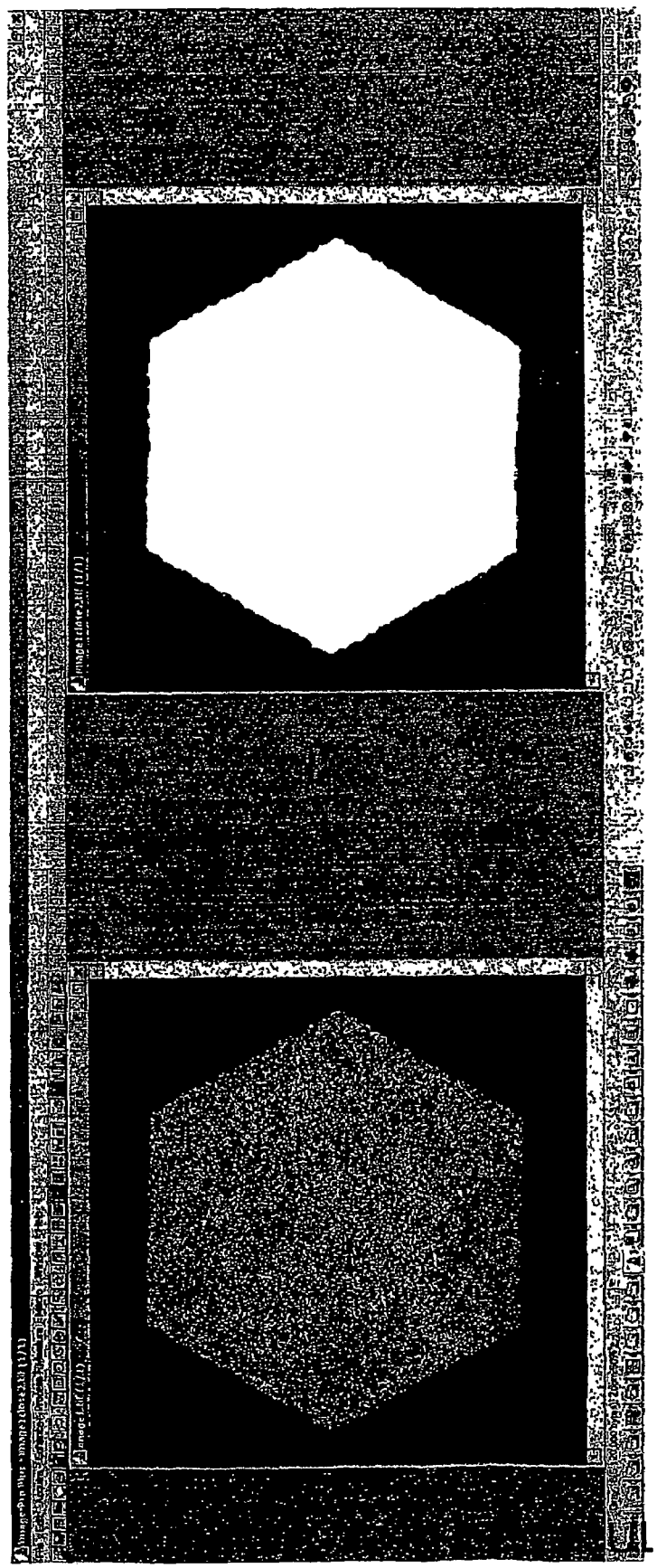
FIG._9

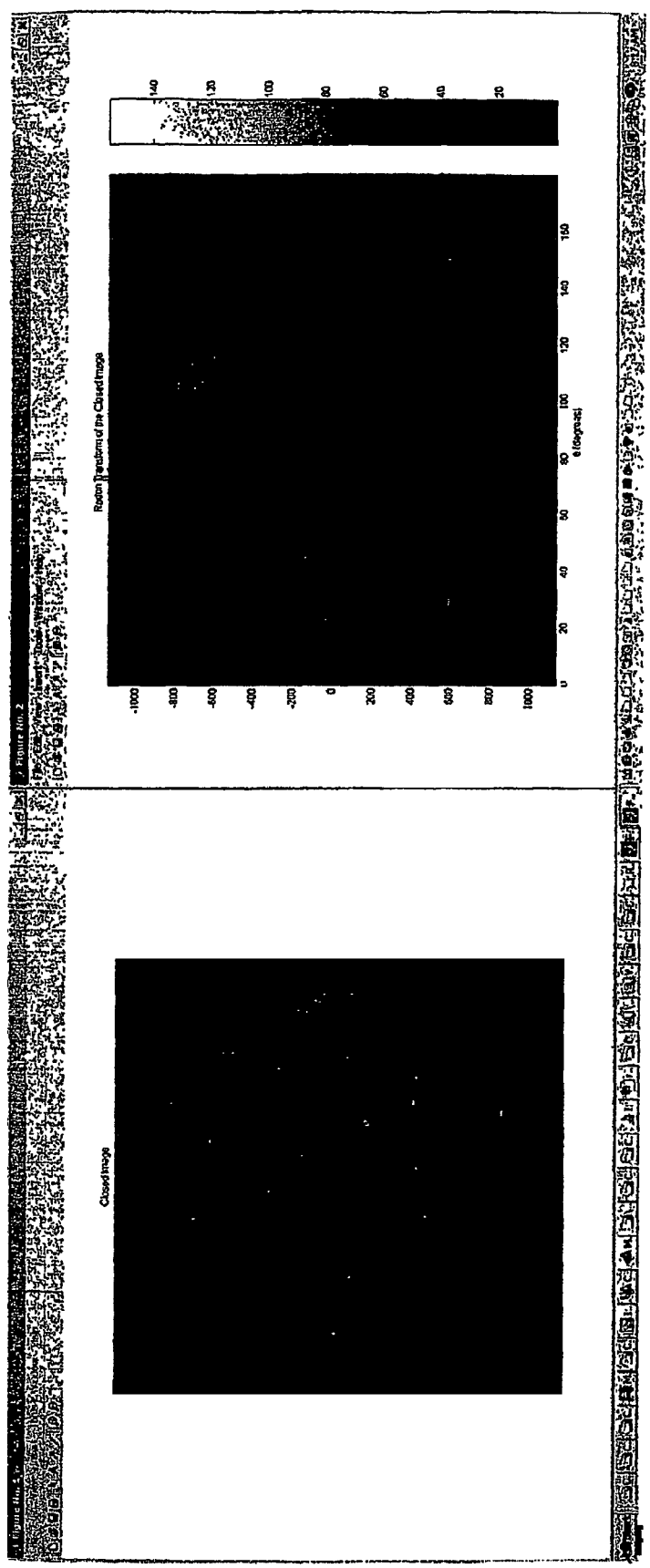
FIG._10

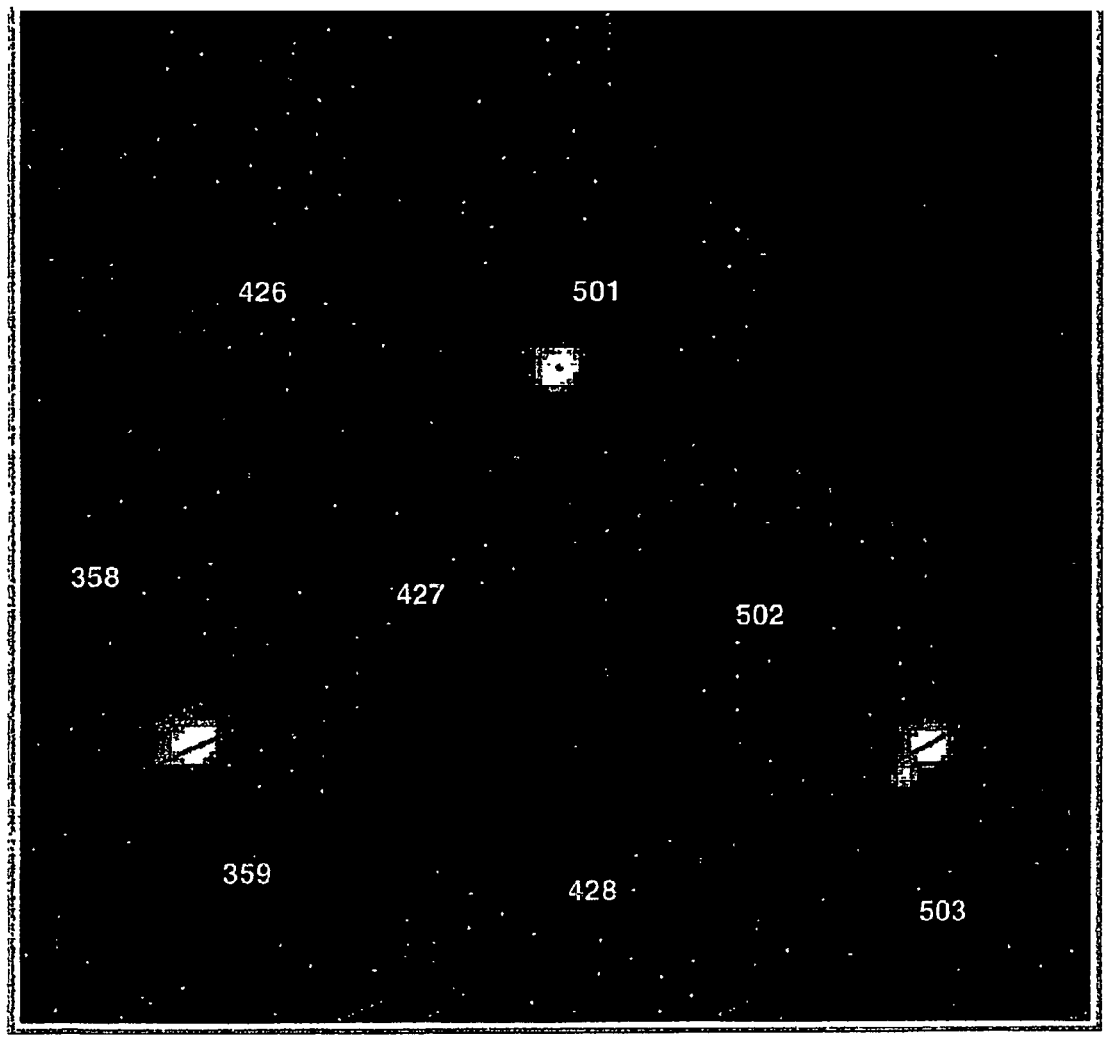
FIG._11

The list of 5 brightest beads for each bead type is used to
(1) Track the intensities of the brightest bead types ➡ maximum at correct registration position
(2) Compute average CV ➡ minimum at correct registration position
| Bead Type | I1 | I2 | I3 | I4 | I5 |
|---|---|---|---|---|---|
| 0 | 1412 | 1170 | 0 | 0 | 0 |
| 2 | 1659 | 0 | 0 | 0 | 0 |
| 5 | 1772 | 1768 | 1747 | 1737 | 1715 |
| 7 | 1762 | 1737 | 1731 | 1709 | 1700 |
| 11 | 1763 | 1759 | 1751 | 1735 | 1731 |
| 19 | 1819 | 1803 | 1788 | 1769 | 1723 |
| 30 | 15357 | 14343 | 13614 | 13539 | 12876 |
| 36 | 1850 | 1827 | 1826 | 1820 | 1780 |
| 42 | 1497 | 0 | 0 | 0 | 0 |
| 43 | 1438 | 0 | 0 | 0 | 0 |
| 54 | 1678 | 1661 | 1573 | 1565 | 1552 |
| 60 | 1650 | 1567 | 1551 | 1509 | 1477 |
| 63 | 1624 | 1585 | 1576 | 1565 | 1563 |
| 67 | 1750 | 0 | 0 | 0 | 0 |
| 69 | 1589 | 1492 | 0 | 0 | 0 |
| 82 | 1930 | 1790 | 1782 | 1760 | 1757 |
| 83 | 1859 | 1763 | 1729 | 1720 | 1719 |
| 84 | 1794 | 1759 | 1749 | 1745 | 1742 |
| 87 | 1807 | 1783 | 1762 | 1757 | 1731 |
| 90 | 1784 | 1752 | 1747 | 1730 | 1723 |
| 99 | 1754 | 1731 | 1727 | 1716 | 1713 |
| 122 | 1855 | 1836 | 1774 | 1742 | 1734 |
| 131 | 1872 | 1811 | 1787 | 1787 | 1783 |
| 133 | 1782 | 1776 | 1763 | 1752 | 1731 |
| 149 | 1953 | 1761 | 1749 | 1741 | 1727 |
Table 1
FIG._12

IMAGE PROCESSING IN MICROSPHERE ARRAYS

This application claims the benefit of U.S. Provisional Application Ser. No. 60/357,213, filed Feb. 14, 2002.

FIELD OF THE INVENTION

The invention relates to the use of a computer system to compare images generated from a randomly ordered array. This system preserves the relative position of each site within the array so that the same site can be compared in different images.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

Of particular use in these sensors are detection mechanisms utilizing luminescence or fluorescence. Recently, the use of optical fibers and optical fiber strands in combination with light absorbing dyes for chemical analytical determinations has undergone rapid development, particularly within the last decade. The use of optical fibers for such purposes and techniques is described by Milanovich et al., "Novel Optical Fiber Techniques For Medical Application", Proceedings of the SPIE 28th Annual International Technical Symposium On Optics and Electro-Optics, Volume 494, 1980; Seitz, W. R., "Chemical Sensors Based On Immobilized Indicators and Fiber Optics" in *C.R.C. Critical Reviews In Analytical Chemistry*, Vol. 19, 1988, pp. 135-173; Wolfbeis, O. S., "Fiber Optical Fluorosensors In Analytical Chemistry" in *Molecular Luminescence Spectroscopy, Methods and Applications* (S. G. Schulman, editor), Wiley & Sons, New York (1988); Angel, S. M., *Spectroscopy* 2 (4):38 (1987); Walt, et al., "Chemical Sensors and Microinstrumentation", *ACS Symposium Series*, Vol. 403, 1989, p. 252, and Wolfbeis, O. S., *Fiber Optic Chemical Sensors*, Ed. CRC Press, Boca Raton, Fla., 1991, 2nd Volume.

When using an optical fiber in an in vitro/in vivo sensor, one or more light absorbing dyes are located near its distal end. Typically, light from an appropriate source is used to illuminate the dyes through the fiber's proximal end. The light propagates along the length of the optical fiber; and a portion of this propagated light exits the distal end and is absorbed by the dyes. The light absorbing dye may or may not be immobilized; may or may not be directly attached to the optical fiber itself; may or may not be suspended in a fluid sample containing one or more analytes of interest; and may or may not be retainable for subsequent use in a second optical determination.

Once the light has been absorbed by the dye, some light of varying wavelength and intensity returns, conveyed through either the same fiber or collection fiber(s) to a detection system where it is observed and measured. The interactions between the light conveyed by the optical fiber and the properties of the light absorbing dye provide an optical basis for both qualitative and quantitative determinations.

Of the many different classes of light absorbing dyes which conventionally are employed with bundles of fiber strands and optical fibers for different analytical purposes are those more common compositions that emit light after absorption termed "fluorophores" and those which absorb light and internally convert the absorbed light to heat, rather than emit it as light, termed "chromophores."

Fluorescence is a physical phenomenon based upon the ability of some molecules to absorb light (photons) at specified wavelengths and then emit light of a longer wavelength and at a lower energy. Substances able to fluoresce share a number of common characteristics: the ability to absorb light energy at one wavelength $\lambda_{ab}$; reach an excited energy state; and subsequently emit light at another light wavelength, $\lambda_{em}$. The absorption and fluorescence emission spectra are individual for each fluorophore and are often graphically represented as two separate curves that are slightly overlapping. The same fluorescence emission spectrum is generally observed irrespective of the wavelength of the exciting light and, accordingly, the wavelength and energy of the exciting light may be varied within limits; but the light emitted by the fluorophore will always provide the same emission spectrum. Finally, the strength of the fluorescence signal may be measured as the quantum yield of light emitted. The fluorescence quantum yield is the ratio of the number of photons emitted in comparison to the number of photons initially absorbed by the fluorophore. For more detailed information regarding each of these characteristics, the following references are recommended: Lakowicz, J. R., *Principles of Fluorescence Spectroscopy*, Plenum Press, New York, 1983; Freifelder, D., *Physical Biochemistry*, second edition, W. H. Freeman and Company, New York, 1982; "Molecular Luminescence Spectroscopy Methods and Applications: Part I" (S. G. Schulman, editor) in *Chemical Analysis*, vol. 77, Wiley & Sons, Inc., 1985; *The Theory of Luminescence*, Stepanov and Gribkovskii, Iliffe Books, Ltd., London, 1968.

In comparison, substances which absorb light and do not fluoresce usually convert the light into heat or kinetic energy. The ability to internally convert the absorbed light identifies the dye as a "chromophore." Dyes which absorb light energy as chromophores do so at individual wavelengths of energy and are characterized by a distinctive molar absorption coefficient at that wavelength. Chemical analysis employing fiber optic strands and absorption spectroscopy using visible and ultraviolet light wavelengths in combination with the absorption coefficient allow for the determination of concentration for specific analyses of interest by spectral measurement. The most common use of absorbance measurement via optical fibers is to determine concentration which is calculated in accordance with Beers' law; accordingly, at a single absorbance wavelength, the greater the quantity of the composition which absorbs light energy at a given wavelength, the greater the optical density for the sample. In this way, the total quantity of light absorbed directly correlates with the quantity of the composition in the sample.

Many of the recent improvements employing optical fiber sensors in both qualitative and quantitative analytical determinations concern the desirability of depositing and/or immobilizing various light absorbing dyes at the distal end of the optical fiber. In this manner, a variety of different optical fiber chemical sensors and methods have been reported for specific analytical determinations and applications such as pH measurement, oxygen detection, and carbon dioxide analyses. These developments are exemplified by the following publications: Freeman, et al., *Anal Chem*. 53:98 (1983);

Lippitsch et al., *Anal. Chem. Acta.* 205:1, (1988); Wolfbeis et al., *Anal. Chem.* 60:2028 (1988); Jordan, et al., *Anal. Chem.* 59:437 (1987); Lubbers et al., *Sens. Actuators* 1983; Munkholm et al., *Talanta* 35:109 (1988); Munkholm et al., *Anal. Chem.* 58:1427 (1986); Seitz, W. R., *Anal. Chem.* 56:16A-34A (1984); Peterson, et al., *Anal. Chem.* 52:864 (1980): Saari, et al., *Anal. Chem.* 54:821 (1982); Saari, et al., *Anal. Chem.* 55:667 (1983); Zhujun et al., *Anal. Chem. Acta.* 160:47 (1984); Schwab, et al., *Anal. Chem.* 56:2199 (1984); Wolfbeis, O. S., "Fiber Optic Chemical Sensors", *Ed. CRC Press, Boca Raton, Fla.*, 1991, 2nd Volume; and Pantano, P., Walt, D. R., *Anal. Chem.*, 481A-487A, Vol. 67, (1995).

More recently, fiber optic sensors have been constructed that permit the use of multiple dyes with a single, discrete fiber optic bundle. U.S. Pat. Nos. 5,244,636 and 5,250,264 to Walt, et al. disclose systems for affixing multiple, different dyes on the distal end of the bundle, the teachings of each of these patents being incorporated herein by this reference. The disclosed configurations enable separate optical fibers of the bundle to optically access individual dyes. This avoids the problem of deconvolving the separate signals in the returning light from each dye, which arises when the signals from two or more dyes are combined, each dye being sensitive to a different analyte, and there is significant overlap in the dyes' emission spectra.

U.S. Ser. Nos. 08/818,199 and 09/151,877 describe array compositions that utilize microspheres or beads on a surface of a substrate, for example on a terminal end of a fiber optic bundle, with each individual fiber comprising a bead containing an optical signature. Since the beads go down randomly, a unique optical signature is needed to "decode" the array; i.e. after the array is made, a correlation of the location of an individual site on the array with the bead or bioactive agent at that particular site can be made. This means that the beads may be randomly distributed on the array, a fast and inexpensive process as compared to either the in situ synthesis or spotting techniques of the prior art. Once the array is loaded with the beads, the array can be decoded, or can be used, with full or partial decoding occurring after testing, as is more fully outlined below.

The use of fiducials for the registration of sequential images has been used in screen printing (U.S. Pat. No. 5,129,155) and in implants in the human body (U.S. Pat. No. 4,991,579) and in various image processing (see U.S. Pat. Nos. 5,245,676 and 5,129,014).

Fiducials also are disclosed in U.S. P No. 60/119,323, filed Feb. 9, 1999, Ser. No. 09/500,555, filed Feb. 9, 2000, Ser. No. 09/636,387, filed Aug. 9, 2000 and Ser. No. 09/925,941, filed Aug. 9, 2001, all of which are expressly incorporated herein by reference.

Accordingly, it is an object of the present invention to provide biosensors comprising random arrays, generally comprising beads distributed at discrete sites on the surface of a substrate, that utilize computer systems and fiducials to allow comparison of sequential data images of the arrays.

SUMMARY OF THE INVENTION

In accordance with the objects outlined above, the present invention provides array compositions comprising a substrate with a surface comprising discrete sites, at least one fiducial, and a population of microspheres comprising at least a first and a second subpopulation. Each subpopulation comprises a bioactive agent, and the microspheres are distributed on said surface. Each subpopulation may optionally comprise a unique optical signature, an identifier binding ligand that will bind a decoder binding ligand such that the identification of the bioactive agent can be elucidated, or both.

In an additional aspect, the invention provides compositions comprising a computer readable memory to direct a computer to function in a specified manner. The computer readable memory comprises an acquisition module for receiving a data image of a random array comprising a plurality of discrete sites, a registration module for registering a data image, and a comparison module for comparing registered data images. Each module comprises computer code for carrying out its function. The registration module may utilize any number of fiducials, including a fiducial fiber when the substrate comprises a fiber optic bundle, a fiducial microsphere, or a fiducial template generated from the random array.

In a further aspect, the invention provides methods of making the array compositions of the invention comprising forming a surface comprising individual sites on a substrate, distributing microspheres on the surface such that the individual sites contain microspheres, and incorporating at least one fiducial onto the surface. When the array has complete rotational freedom, at least two fiducials are preferred in the array to allow for correction of rotation.

In an additional aspect, the invention provides methods for comparing separate data images of a random array. The methods comprise using a computer system to register a first data image of the random array to produce a registered first data image, using the computer system to register a second data image of the random array to produce a registered second data image, and comparing the first and the second registered data images to determine any differences between them.

In a further aspect, the invention provides methods of decoding a random array composition comprising providing a random array composition as outlined herein. A first plurality of decoding binding ligands is added to the array composition and a first data image is created. A fiducial is used to generate a first registered data image. A second plurality of decoding binding ligands is added to the array composition and a second data image is created. The fiducial is used to generate a second registered data image. A computer system is used to compare the first and the second registered data image to identify the location of at least two bioactive agents.

In an additional aspect, the invention provides methods of determining the presence of a target analyte in a sample. The methods comprise acquiring a first data image of a random array composition, and registering the first data image to create a registered first data image. The sample is then added to the random array and a second data image is acquired from the array. The second data image is registered to create a registered second data image. Then the first and the second registered data images are compared to determine the presence or absence of the target analyte. Optionally, the data acquisition may be at different wavelengths.

In a further aspect, the present invention provides methods for preprocessing or prefiltering signal data comprising acquiring a data image from an array of the invention, and determining the similarity of a first signal from at least one array site to a reference signal to determine whether the site comprises a candidate bead.

In a further aspect, the invention provides for methods for registering an analytical image of a microsphere array comprising providing a hybridization intensity image as outlined herein. After the microsphere array is decoded, a registration grid is computed based on known locations of bioactive agents on the microspheres obtained from the decoding step. The sample is added to the microsphere array and a hybridization intensity image is acquired from the array. Bright bead types are distributed throughout the array to serve as fiducials. The registration grid is overlaid on to the image and then the registration grid is aligned so that the identity of the signal intensity at each grid location for each bead type within the array is ascertained. Once the correct position of the grid is obtained, each core is assigned a number so that the correct placement of the grid can be made for further sequential images.

BRIEF DESCRIPTION OF THE DRAWINGS

FIG. 1 illustrates a fiber optic bundle with fiducial fibers.

FIG. 2 illustrates the components of a multi-multi fiber including fiducial markers, optical fiber bundles (multi fiber) and the components of a single optical fiber (mono fiber).

FIG. 3 exemplifies the signal obtained when detecting a signal with multiple different channels (C1, C2, C3 and C4). A. Signal detected when no bleed-through signal is detected. B. Signal detected when bleed-through signal is detected.

FIG. 4 depicts the "similarity funnel" or "vicinity funnel" (threshold) of the vector v, obtained upon comparing a reference signal with a theoretical signal. If a vector falls inside this funnel, it is considered "similar".

FIG. 5 depicts a plurality of similarity funnels obtained upon comparing multiple reference signals with corresponding theoretical signals. If a vector (core) falls within any of these four funnels (in the case of four color channels), it is labeled a "candidate bead"; otherwise it will be rejected.

FIGS. 6A and 6B depict preferred processing schemes.

FIG. 7 depicts a preferred embodiment of the invention.

FIGS. 8A and 8B depict a preferred embodiment of the invention.

FIG. 9 depicts a preferred embodiment of the invention.

FIG. 10 depicts a preferred embodiment of the invention.

FIG. 11 depicts an analytical image obtained using bright bead types throughout the hybridization intensity image to serve as fiducials.

FIG. 12 depicts a list of 5 brightest bead types used to track the intensities of the brightest bead types at various positions during alignment of the grid. The intensities are a maximum at the correct registration position and the average cv is a minimum at the correct registration position.

DETAILED DESCRIPTION OF THE INVENTION

The present invention is directed to the use of randomly ordered arrays comprising a bead-based analytic chemistry system in which beads, also termed microspheres, carrying different chemical functionalities are distributed on a substrate comprising a patterned surface of discrete sites that can bind the individual microspheres. The beads are generally put onto the substrate randomly, i.e. each bead goes down arbitrarily or indiscriminately on to a site. This allows the synthesis of the candidate agents (i.e. compounds such as nucleic acids and antibodies) to be divorced from their placement on an array, i.e. the candidate agents may be synthesized on the beads, or on a different substrate and then put onto the beads, and then the beads are randomly distributed on a patterned surface.

However, the random placement of the beads means that all or part of the array must be "decoded" after synthesis; that is, after the array is made, a correlation of the location of an individual site on the array with the bead or candidate agent at that particular site can be made. This encoding/decoding can be done in a number of ways, as is generally described in Ser. Nos. 60/090,473; 09/189,543; 08/944,850; 08/818,199; 09/151,877; and 08/851,203, all of which are hereby expressly incorporated by reference in their entirety. These methods include: (1) "encoding" the beads with unique optical signatures, generally fluorescent dyes, that can be used to identify the chemical functionality on any particular bead; (2) using a decoding binding ligand (DBL), generally directly labeled, that binds to either the bioactive agent or to identifier binding ligands (IBLs) attached to the beads; (3) the use of positional decoding, for example by either targeting the placement of beads (for example by using photoactivatible or photo cleavable moieties to allow the selective addition of beads to particular locations), or by using either sub-bundles or selective loading of the sites, as are more fully outlined below; (4) the use of selective decoding, wherein only those beads that bind to a target are decoded; or (5) combinations of any of these. In some cases, as is more fully outlined below, this decoding may occur for all the beads, or only for those that bind a particular target analyte. Similarly, this may occur either prior to or after addition of a target analyte.

This means that the beads may be randomly distributed on the array, a fast and inexpensive process as compared to either the in situ synthesis or spotting techniques of the prior art.

Once the identity (i.e. the actual agent) and location of each microsphere in the array has been fixed, the array is exposed to samples containing the target analytes, although as outlined below, this can be done prior to, during or after the assay as well. The target analytes will bind to the bioactive agents as is more fully outlined below, and results in a change in an optical signal of a particular bead.

The present invention is directed to compositions and methods that allow comparisons of sequential data images taken during decoding and assay analysis. That is, in the broadest sense, the invention provides computer systems comprising processors and computer readable memory that allow the storage and analysis of multiple captured images of the same array, whether to compare a decoding image and an experimental image, several experimental images or several decoding images. That is, a first data image is taken of a random array, and using either a fiducial template or an external fiducial, the data image is registered. A second data image is then taken and registered, and the two registered data images can now be compared, as is more fully outlined below.

In a preferred embodiment, the present invention provides a variety of "registration" techniques that allow the comparison of a variety of these images in a uniform and reliable way. That is, in order to compare multiple data images from an array comprising a plurality of unique sites, it is important that the correct individual sites be compared during analysis. In a highly complex and small system, methods are needed to ensure that a first site in a first data image is correctly matched to the first site in a second data image. Accordingly, the present invention provides the incorporation of one or more reference features, also referred to herein as "markers" or "fiducials" or "registration points", that allow this registration from image to image. It is generally preferred to have a number of spatially separated fiducials so that small amounts of skew and reduction/enlargement can be determined and taken into account.

As is further described below, these fiducials can take a number of forms. For example, when the random array comprises beads, the fiducial may be a bead with a unique optical signature or other characteristic (FIG. 1). When the random array comprises a fiber optic bundle, the fiducial may be a fiber element with a unique shape or optical properties. Alternatively, the substrate may have other types of physical fiducials, such one or more defined edges that have characteristic optical properties that can be either spaced along the edge(s) or comprise the entire edge (FIG. 2). Alternatively, the fiducials may be an inherent characteristic of the array; for example, small irregularities in the sites (features) of the array can be exploited to serve as fiducials, generating a "fiducial template".

Accordingly, the present invention provides random array compositions comprising at least a first substrate with a surface comprising individual sites. By "random" array herein is meant an array that is manufactured under conditions that results in the identification of the agent in at least some, if not all, of the sites of the array being initially unknown; that is, each agent is put down arbitrarily on a site of the array in a generally non-reproducible manner. What is important in random arrays, and what makes the present invention so useful, is that random arrays generally require at least one, and generally several "decoding" steps that produce data images that must be compared. In addition, while the techniques of the invention can be used on a variety of random arrays, the discussion below is directed to the use of arrays comprising microspheres that are laid down randomly on a surface comprising discrete sites. However, as will be appreciated by those in the art, other types of random arrays, i.e. those not containing beads, may also utilize the methods of the invention.

By "array" herein is meant a plurality of candidate agents in an array format; the size of the array will depend on the composition and end use of the array. Arrays containing from about 2 different bioactive agents (i.e. different beads) to many millions can be made, with very large fiber optic arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays (all numbers are per $cm^2$) are from about 10,000,000 to about 2,000,000,000, with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 µm or less (with beads of 200 nm possible) can be used, and very small fibers are known, it is possible to have as many as 40,000 or more (in some instances, 1 million) different fibers and beads in a 1 $mm^2$ fiber optic bundle, with densities of greater than 25,000,000 individual beads and fibers (again, in some instances as many as 100 million) per 0.5 $cm^2$ obtainable.

By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon®, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics.

In addition, as is more fully outlined below, the substrate may include a coating, edging or sheath of material, generally detectable, that defines a substrate edge that may serve as one or more fiducials.

In a preferred embodiment, the substrate is an optical fiber bundle or array, as is generally described in U.S. Ser. Nos. 08/944,850 and 08/519,062, PCT US98/05025, and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable without intentionally treating the preformed unitary array with agents that separate them, for example treating a preformed array susceptible to acid with an acid such that the interstitial material is etched and thus the individual cores can be separated. However, absent these intentional treatments, one strand generally cannot be physically separated at any point along its length from another fiber strand.

At least one surface of the substrate is modified to contain discrete, individual sites for later association of microspheres. These sites may also be referred to in some embodiments as "features". These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, physical alterations are made in a surface of the substrate to produce the sites. In a preferred embodiment, the substrate is a fiber optic bundle and the surface of the substrate is a terminal end of the fiber bundle, as is generally described in Ser. No. 08/818,199 and 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

In a preferred embodiment, the compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each bioactive agent; preferred embodiments utilize a plurality of beads of each type.

By "microspheres" or "beads" or "particles" or grammatical equivalents herein is meant small discrete particles. The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphited, titanium dioxide, latex or cross-linked dextrans such as Sepharose, cellulose, nylon, cross-linked micelles and teflon may all be used. *"Microsphere Detection Guide"* from Bangs Laboratories, Fishers Ind. is a helpful guide.

The beads need not be spherical; irregular particles may be used. In addition, the beads may be porous, thus increasing the surface area of the bead available for either bioactive agent attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments larger or smaller beads may be used.

It should be noted that a key component of the invention is the use of a substrate/bead pairing that allows the association or attachment of the beads at discrete sites on the surface of the substrate, such that the beads do not move during the course of the assay.

Each microsphere comprises a bioactive agent, although as will be appreciated by those in the art, there may be some microspheres which do not contain a bioactive agent, depending the on the synthetic methods. By "candidate bioactive agent" or "bioactive agent" or "chemical functionality" or "binding ligand" herein is meant as used herein describes any molecule, e.g., protein, oligopeptide, small organic molecule, coordination complex, polysaccharide, polynucleotide, etc. which can be attached to the microspheres of the invention. It should be understood that the compositions of the invention have two primary uses. In a preferred embodiment, as is more fully outlined below, the compositions are used to detect the presence of a particular target analyte; for example, the presence or absence of a particular nucleotide sequence or a particular protein, such as an enzyme, an antibody or an antigen. In an alternate preferred embodiment, the compositions are used to screen bioactive agents, i.e. drug candidates, for binding to a particular target analyte.

Bioactive agents encompass numerous chemical classes, though typically they are organic molecules, preferably small organic compounds having a molecular weight of more than 100 and less than about 2,500 daltons. Bioactive agents comprise functional groups necessary for structural interaction with proteins, particularly hydrogen bonding, and typically include at least an amine, carbonyl, hydroxyl or carboxyl group, preferably at least two of the functional chemical groups. The bioactive agents often comprise cyclical carbon or heterocyclic structures and/or aromatic or polyaromatic structures substituted with one or more of the above functional groups. Bioactive agents are also found among biomolecules including peptides, nucleic acids, saccharides, fatty acids, steroids, purines, pyrimidines, derivatives, structural analogs or combinations thereof. Particularly preferred are nucleic acids and proteins.

Bioactive agents can be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification and/or amidification to produce structural analogs.

In a preferred embodiment, the bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In one preferred embodiment, the bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In a preferred embodiment, a library of bioactive agents are used. The library should provide a sufficiently structurally diverse population of bioactive agents to effect a probabilistically sufficient range of binding to target analytes. Accordingly, an interaction library must be large enough so that at least one of its members will have a structure that gives it affinity for the target analyte. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. Thus, in a preferred embodiment, at least $10^6$, preferably at least $10^7$, more preferably at least $10^8$ and most preferably at least $10^9$ different bioactive agents are simultaneously analyzed in the subject methods. Preferred methods maximize library size and diversity.

In a preferred embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the bioactive agents are nucleic acids (generally called "probe nucleic acids" or "candidate probes" herein). By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49 (10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al., J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoramidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365: 566 (1993); Carlsson, et al, Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleosides & Nucleotides, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169-176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments; for example, PNA is particularly preferred. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole and nitroindole, etc.

As described above generally for proteins, nucleic acid bioactive agents may be naturally occurring nucleic acids, random nucleic acids, or "biased" random nucleic acids. For example, digests of procaryotic or eukaryotic genomes may be used as is outlined above for proteins.

In general, probes of the present invention are designed to be complementary to a target sequence (either the target analyte sequence of the sample or to other probe sequences, as is described herein), such that hybridization of the target and the probes of the present invention occurs. This complementarity need not be perfect; there may be any number of base pair mismatches that will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under the selected reaction conditions. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10°C lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30°C for short probes (e.g. 10 to 50 nucleotides) and at least about 60°C for long probes (e.g. greater than 50 nucleotides). Stringent conditions may also be achieved with the addition of destabilizing agents such as formamide. In another embodiment, less stringent hybridization conditions are used; for example, moderate or low stringency conditions may be used, as are known in the art; see Maniatis and Ausubel, supra, and Tijssen, supra.

The term "target sequence" or grammatical equivalents herein means a nucleic acid sequence on a single strand of nucleic acid. The target sequence may be a portion of a gene, a regulatory sequence, genomic DNA, cDNA, RNA including mRNA and rRNA, or others. It may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. As is outlined more fully below, probes are made to hybridize to target sequences to determine the presence or absence of the target sequence in a sample. Generally speaking, this term will be understood by those skilled in the art.

In a preferred embodiment, the bioactive agents are organic chemical moieties, a wide variety of which are available in the literature.

In a preferred embodiment, each bead comprises a single type of bioactive agent, although a plurality of individual bioactive agents are preferably attached to each bead. Similarly, preferred embodiments utilize more than one microsphere containing a unique bioactive agent; that is, there is redundancy built into the system by the use of subpopulations of microspheres, each microsphere in the subpopulation containing the same bioactive agent.

As will be appreciated by those in the art, the bioactive agents may either be synthesized directly on the beads, or they may be made and then attached after synthesis. In a preferred embodiment, linkers are used to attach the bioactive agents to the beads, to allow both good attachment, sufficient flexibility to allow good interaction with the target molecule, and to avoid undesirable binding reactions.

In a preferred embodiment, the bioactive agents are synthesized directly on the beads. As is known in the art, many classes of chemical compounds are currently synthesized on solid supports, such as peptides, organic moieties, and nucleic acids. It is a relatively straightforward matter to adjust the current synthetic techniques to use beads.

In a preferred embodiment, the bioactive agents are synthesized first, and then covalently attached to the beads. As will be appreciated by those in the art, this will be done depending on the composition of the bioactive agents and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

These functional groups can be used to add any number of different candidate agents to the beads, generally using known chemistries. For example, candidate agents containing carbohydrates may be attached to an amino-functionalized support; the aldehyde of the carbohydrate is made using standard techniques, and then the aldehyde is reacted with an amino group on the surface. In an alternative embodiment, a sulfhydryl linker may be used. There are a number of sulfhydryl reactive linkers known in the art such as SPDP, maleimides, α-haloacetyls, and pyridyl disulfides (see for example the 1994 Pierce Chemical Company catalog, technical section on cross-linkers, pages 155-200, incorporated herein by reference) which can be used to attach cysteine containing proteinaceous agents to the support. Alternatively, an amino group on the candidate agent may be used for attachment to an amino group on the surface. For example, a large number of stable bifunctional groups are well known in the art, including homobifunctional and heterobifunctional linkers (see Pierce Catalog and Handbook, pages 155-200). In an additional embodiment, carboxyl groups (either from the surface or from the candidate agent) may be derivatized using well known linkers (see the Pierce catalog). For example, carbodiimides activate carboxyl groups for attack by good nucleophiles such as amines (see Torchilin et al., *Critical Rev. Therapeutic Drug Carrier Systems*, 7(4):275-308 (1991), expressly incorporated herein). Proteinaceous candidate agents may also be attached using other techniques known in the art, for example for the attachment of antibodies to polymers; see Slinkin et al., *Bioconi. Chem.* 2:342-348 (1991); Torchilin et al., supra; Trubetskoy et al., *Bioconi. Chem.* 3:323-327 (1992); King et al., *Cancer Res.* 54:6176-6185 (1994); and Wilbur et al., *Bioconjugate Chem.* 5:220-235 (1994), all of which are hereby expressly incorporated by reference). It should be understood that the candidate agents may be attached in a variety of ways, including those listed above. What is important is that manner of attachment does not significantly alter the functionality of the candidate agent; that is, the candidate agent should be attached in such a flexible manner as to allow its interaction with a target.

Specific techniques for inunobilizing enzymes on microspheres are known in the prior art. In one case, $NH_2$ surface chemistry microspheres are used. Surface activation is achieved with a 2.5% glutaraldehyde in phosphate buffered saline (10 mM) providing a pH of 6.9. (138 mM NaCl, 2.7 mM, KCl). This is stirred on a stir bed for approximately 2 hours at room temperature. The microspheres are then rinsed with ultrapure water plus 0.01% tween 20 (surfactant) –0.02%, and rinsed again with a pH 7.7 PBS plus 0.01% tween 20. Finally, the enzyme is added to the solution, preferably after being prefiltered using a 0.45 μm amicon micropure filter.

In some embodiments, the microspheres may additionally comprise identifier binding ligands for use in certain decoding systems. By "identifier binding ligands" or "IBLs" herein is meant a compound that will specifically bind a corresponding decoder binding ligand (DBL) to facilitate the elucidation of the identity of the bioactive agent attached to the bead. That is, the IBL and the corresponding DBL form a binding partner pair. By "specifically bind" herein is meant that the IBL binds its DBL with specificity sufficient to differentiate between the corresponding DBL and other DBLs (that is, DBLs for other IBLs), or other components or contaminants of the system. The binding should be sufficient to remain bound under the conditions of the decoding step, including wash steps to remove non-specific binding. In some embodiments, for example when the IBLs and corresponding DBLs are proteins or nucleic acids, the dissociation constants of the IBL to its DBL will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ being particularly preferred.

IBL-DBL binding pairs are known or can be readily found using known techniques. For example, when the IBL is a protein, the DBLs include proteins (particularly including antibodies or fragments thereof (FAbs, etc.)) or small molecules, or vice versa (the IBL is an antibody and the DBL is a protein). Metal ion—metal ion ligands or chelators pairs are also useful. Antigen-antibody pairs, enzymes and substrates or inhibitors, other protein-protein interacting pairs, receptor-ligands, complementary nucleic acids, and carbohydrates and their binding partners are also suitable binding pairs. Nucleic acid—nucleic acid binding proteins pairs are also useful. Similarly, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptomers" can be developed for binding to virtually any target; such a aptomer-target pair can be used as the IBL-DBL pair. Similarly, there is a wide body of literature relating to the development of binding pairs based on combinatorial chemistry methods.

In a preferred embodiment, the IBL is a molecule whose color or luminescence properties change in the presence of a selectively-binding DBL. For example, the IBL may be a fluorescent pH indicator whose emission intensity changes with pH. Similarly, the IBL may be a fluorescent ion indicator, whose emission properties change with ion concentration.

Alternatively, the IBL is a molecule whose color or luminescence properties change in the presence of various solvents. For example, the IBL may be a fluorescent molecule such as an ethidium salt whose fluorescence intensity increases in hydrophobic environments. Similarly, the IBL may be a derivative of fluorescein whose color changes between aqueous and nonpolar solvents.

In one embodiment, the DBL may be attached to a bead, i.e. a "decoder bead", that may carry a label such as a fluorophore.

In a preferred embodiment, the IBL-DBL pair comprise substantially complementary single-stranded nucleic acids. In this embodiment, the binding ligands can be referred to as "identifier probes" and "decoder probes". Generally, the identifier and decoder probes range from about 4 basepairs in length to about 1000, with from about 6 to about 100 being preferred, and from about 8 to about 40 being particularly preferred. What is important is that the probes are long enough to be specific, i.e. to distinguish between different IBL-DBL pairs, yet short enough to allow both a) dissociation, if necessary, under suitable experimental conditions, and b) efficient hybridization.

In a preferred embodiment, as is more fully outlined below, the IBLs do not bind to DBLs. Rather, the IBLs are used as identifier moieties ("IMs") that are identified directly, for example through the use of mass spectroscopy.

In a preferred embodiment, the microspheres comprise an optical signature that can be used to identify the attached bioactive agent, as is generally outlined in U.S. Ser. Nos. 08/818,199 and 09/151,877, both of which are hereby incorporated by reference. That is, each subpopulation of microspheres comprise a unique optical signature or optical tag that can be used to identify the unique bioactive agent of that subpopulation of microspheres; a bead comprising the unique optical signature may be distinguished from beads at other locations with different optical signatures. As is outlined herein, each bioactive agent will have an associated unique optical signature such that any microspheres comprising that bioactive agent will be identifiable on the basis of the signature. As is more fully outlined below, it is possible to reuse or duplicate optical signatures within an array, for example, when another level of identification is used, for example when beads of different sizes are used, or when the array is loaded sequentially with different batches of beads.

In a preferred embodiment, the optical signature is generally a mixture of reporter dyes, preferably fluorescent. By varying both the composition of the mixture (i.e. the ratio of one dye to another) and the concentration of the dye (leading to differences in signal intensity), matrices of unique tags may be generated. This may be done by covalently attaching the dyes to the surface of the beads, or alternatively, by entrapping the dye within the bead. The dyes may be chromophores or phosphors but are preferably fluorescent dyes, which due to their strong signals provide a good signal-to-noise ratio for decoding. Suitable dyes for use in the invention include, but are not limited to, fluorescent lanthanide complexes, including those of Europium and Terbium, fluorescein, rhodamine, tetramethylrhodamine, eosin, erythrosin, coumarin, methylcoumarins, pyrene, Malacite green, stilbene, Lucifer Yellow, CASCADE BLUE® dye, TEXAS RED® dye, and others described in the 1989-1991 Molecular Probes Handbook by Richard P. Haugland, hereby expressly incorporated by reference.

In a preferred embodiment, the encoding can be accomplished in a ratio of at least two dyes, although more encoding dimensions may be added in the size of the beads, for example. In addition, the labels are distinguishable from one another; thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the bioactive agents, using functional groups on the surface of the beads. As will be appreciated by those in the art, these attachments are done to minimize the effect on the dye.

In a preferred embodiment, the dyes are non-covalently associated with the beads, generally by entrapping the dyes in the bead matrix or pores of the beads. Fluorescent dyes are generally preferred because the strength of the fluorescent signal provides a better signal-to-noise ratio when decoding. Additionally, encoding in the ratios of the two or more dyes, rather than single dye concentrations, is preferred since it provides insensitivity to the intensity of light used to interrogate the reporter dye's signature and detector sensitivity.

In one embodiment, the dyes are added to the bioactive agent, rather than the beads, although this is generally not preferred.

In one embodiment, the microspheres do not contain an optical signature.

In a preferred embodiment, the present invention does not rely solely on the use of optical properties to decode the arrays. However, as will be appreciated by those in the art, it is possible in some embodiments to utilize optical signatures as an additional coding method, in conjunction with the present system. Thus, for example, as is more fully outlined below, the size of the array may be effectively increased while using a single set of decoding moieties in several ways, one of which is the use of optical signatures one some beads. Thus, for example, using one "set" of decoding molecules, the use of two populations of beads, one with an optical signature and one without, allows the effective doubling of the array size. The use of multiple optical signatures similarly increases the possible size of the array.

In a preferred embodiment, each subpopulation of beads comprises a plurality of different identifier binding ligands ("IBLs"). By using a plurality of different IBLs to encode each bioactive agent, the number of possible unique codes is substantially increased. That is, by using one unique IBL per bioactive agent, the size of the array will be the number of unique IBLs (assuming no "reuse" occurs, as outlined below). However, by using a plurality of different IBLs per bead, n, the size of the array can be increased to $2^n$, when the presence or absence of each IBL is used as the indicator. For example, the assignment of 10 IBLs per bead generates a 10 bit binary code, where each bit can be designated as "1" (IBL is present) or "0" (IBL is absent). A 10 bit binary code has $2^{10}$ possible variants However, as is more fully discussed below, the size of the array may be further increased if another parameter is included such as concentration or intensity; thus for example, if two different concentrations of the IBL are used, then the array size increases as $3^n$. Thus, in this embodiment, each individual bioactive agent in the array is assigned a combination of IBLs, which can be added to the beads prior to the addition of the bioactive agent, after, or during the synthesis of the bioactive agent, i.e. simultaneous addition of IBLs and bioactive agent components.

Alternatively, when the bioactive agent is a polymer of different residues, i.e. when the bioactive agent is a protein or nucleic acid, the combination of different IBLs can be used to elucidate the sequence of the protein or nucleic acid.

Thus, for example, using two different IBLs (IBL1 and IBL2), the first position of a nucleic acid can be elucidated: for example, adenosine can be represented by the presence of both IBL1 and IBL2; thymidine can be represented by the presence of IBL1 but not IBL2, cytosine can be represented by the presence of IBL2 but not IBL1, and guanosine can be represented by the absence of both. The second position of the nucleic acid can be done in a similar manner using IBL3 and IBL4; thus, the presence, of IBL1, IBL2, IBL3 and IBL4 gives a sequence of AA; IBL1, IBL2, and IBL3 shows the sequence AT; IBL1, IBL3 and IBL4 gives the sequence TA, etc. The third position utilizes IBL5 and IBL6, etc. In this way, the use of 20 different identifiers can yield a unique code for every possible 10-mer.

The system is similar for proteins but requires a larger number of different IBLs to identify each position, depending on the allowed diversity at each position. Thus for example, if every amino acid is allowed at every position, five different IBLs are required for each position. However, as outlined above, for example when using random peptides as the bioactive agents, there may be bias built into the system; not all amino acids may be present at all positions, and some positions may be preset; accordingly, it may be possible to utilize four different IBLs for each amino acid.

In this way, a sort of "bar code" for each sequence can be constructed; the presence or absence of each distinct IBL will allow the identification of each bioactive agent.

In addition, the use of different concentrations or densities of IBLs allows a "reuse" of sorts. If, for example, the bead comprising a first agent has a 1× concentration of IBL, and a second bead comprising a second agent has a 10× concentration of IBL, using saturating concentrations of the corresponding labelled DBL allows the user to distinguish between the two beads.

In a preferred embodiment, the compositions of the invention further comprise at least one fiducial. By "fiducial" or "marker" or "registration point" herein is meant a physical reference feature or characteristic that allows precise comparisons of sequential data images of an array. The use of fiducials is useful for a variety of reasons. In general, the assays involve monitoring of objects, i.e. bioactive agents, located at spatially distinct locations (features) over the course of several data image frames taken over time. Any shifting that occurs from frame to frame complicates the analysis of the agents. By incorporating permanent fiducials into the assay structure, each data image can be aligned, either manually or automatically, to allow accurate comparison of the images, and control for translation (i.e. a shift in an X-Y direction) and/or rotation as well as reduction or enlargement of the image. However, it should be noted that fiducials can be used that are based on endogenous array characteristics such as fiducial templates (described herein) or the use of array components (inherent bright beads as described below). In addition, when fluorescence based assays are used (either for decoding or analyte assaying or both), in any given image, a particular region or feature may or may not emit fluorescence, depending on the label characteristics and the wavelength being interrogated, or the presence or absence of an analyte or DBL, etc. The presence of fluorescence is detected as a positive change in feature intensity with respect to the background intensity, which is then used to draw a software "segment" over the core. In situations where the core is dark, i.e. no fluorescence is detected at that particular feature, it is difficult to accurately draw the segment over the core.

Accordingly, in a preferred embodiment, at least one fiducial is incorporated into the array. In a preferred embodiment, a plurality of fiducials are used, with the ideal number depending on the size of the array (i.e. features per fiducial), the density of the array, the shape of the array, the irregularity of the array, etc. In general, at least three non-linear fiducials are used; that is, three fiducials that define a plane (i.e. are not in a line) are used. In addition, it is preferred to have at least one of the fiducials be either on or close to the periphery of the array.

In a preferred embodiment, the substrate is a fiber optic bundle and the fiducial is a fiducial fiber. As will be appreciated by those in the art, the characteristics of a fiducial fiber may vary widely. For example, in a preferred embodiment, the fiducial fibers may have unique or special optical properties; for example, fiducial fibers made of stock glass that exhibits broad fluorescence across the visible range of the spectrum; glasses are available in a wide range of compositions, and often possess intrinsic fluorescence due to the presence of impurities or dopants in the glass material. In a preferred embodiment, the fiducial fibers may have a different shape or size, or both, from the other fibers of the array. In addition, as is true for all the fiducial techniques herein, it is often preferred to have different fiducials have different characteristics, i.e. asymmetry among the fiducials, to allow for an extra level of registration. For example, in an square array format with fiducials at the corners, one of the four fiducials could be of a different shape or size than the other three or positionally offset.

The fiducial fibers may each be labeled with the sane or with different labels. In a preferred embodiment a fiber is coated with a single label. In addition, multiple fibers to be incorporated into an array are labeled with the same label. In an alternative embodiment, each of a plurality of fiducial fibers is labeled with a different or discrete label. In a preferred embodiment a fiducial fiber comprises a detectable label, such as a dye, fluorescent organic dye or fluorescent inorganic particles such as quantum dots.

Arrays comprising fiducial fibers are generally made in a variety of ways.

In one embodiment, the fiber is doped with fluorescent organic dyes or fluorescent inorganic particles such as quantum dots at the melting stage, prior to the machining of the glass into rods for drawing.

In a preferred embodiment, the glass rod material is dipped into or covered with a solution of a label such as a fluorescent dopant material. Preferred embodiments utilize inorganic nanoparticles (quantum dots) as they are small in size, exhibit high fluoresence quantum efficiencies, and are extremely photostable over long period of time (i.e. resistant to photobleaching). The fluorescent characteristics of quantum dots are known to be directly related to the size of the particles. In a preferred embodiment, a polydisperse collection of particles is employed to give rise to broad absorbtive and emissive properties.

In another embodiment predoped fibers such as terbium-doped fibers are used as a foundation for the fiducial, and a label such as a fluorescent particle is added to the exterior of these core glasses to give rise to a fiber that exhibits fluorescent properties of both the internal and external dopants.

Following the coating of the outside of either of the above-described core bars with a label, the bar is then inserted into a cladding tube of lower refractive index and drawn. By cladding the coated fiber, excitation light can be made to propagate down the core, exciting any fluorescent material present either in the core itself or, in this case, at the interface between the core and the clad. The fluorescence is then coupled into the core and light-guided back up the core to the proximal face of the fiber where it is detected, for example by a CCD camera.

In an alternative embodiment each of a plurality of fibers are incorporated into an array and each is coated with a different label. By increasing the number of labels incorporated into fiducial fibers, the number and complexity of labels and/or registers increases.

In a preferred embodiment, the fiducial is a fiducial bead of the random array. Similar to the fiducial fibers, fiducial beads may be added to the random array in any position. Thus, for example, a few fiducial beads may be added to the array prior to or simultaneously with the addition of the beads comprising bioactive agents. In this case the fiducial beads may go down randomly on the array. Alternatively, when wells are used, targeted addition of fiducial beads may be done; for example, by creating larger wells in defined locations (for example by using a few larger fibers and etching techniques), large fiducial beads may be laid down in certain sites. As above for fiducial fibers, the detectable properties of the fiducial beads may be different than the properties of the beads comprising agents. In addition, when randomly laid down fiducial beads are used, it should be noted that an advantage of the resulting array is that the fiducial pattern is essentially a "signature" of the individual array. That is, since the likelihood of two arrays containing the same spatial arrangement of fiducial beads is very low, individual arrays can be visually distinguished, serving as a sort of internal "label" for the array.

In another embodiment, the marker bead comprises no label, while the remaining beads or microspheres are labeled. Thus, the absence of a label serves to identify the marker bead on the array.

In a preferred embodiment an array comprises at least one marker bead, although more than one marker bead is particularly preferred.

The marker bead(s) can be added to the substrate or array at any time prior to, simultaneously with or following the addition of other microspheres.

In one embodiment the method provides a scheme to ensure the correct association of analytical signals and their location on an array, i.e. their addresses derived from randomly arrays.

This method includes loading wells, i.e. fibers, with a small number of addressed fiducial beads among the total pool of beads used in a given experiment. Such fiducial beads would be labeled or dyed to have a predefined fluorescent signal in the same channel as the analytical signal. These beads would also contain a defined address encoded in the same manner as the addresses on the analytical beads that form the array. For instance, if the array were addressed by a DNA adapter code or IBL/DBL, then the fiducial beads would contain a distinct adapter address. Once the decoding is complete and analytical values are extracted for each bead, two expectations would have to be fulfilled if the data are correctly associated: (i) the fiducial bead address would be represented in the present codes; and (ii) these addresses would be associated with a mean signal value consistent with the dye loaded in the fiducial beads.

Multiple types of fiducial addressed beads could be included. These might contain other features, for instance, a graded series of dye intensities that would allow one to have a signal calibration curve built into each array This method offers certain advantages over methods that require discrete steps of extracting a fiducial image and aligning this image with the image obtained from an analytical. The current method ensures that analytical signals and their addresses do not become dissociated during multiple steps of analysis. That is, because analytical signals and their addresses could conceivably become disassociated in stages following the image acquisition, e.g., from subsequent software and database errors, one would like to have information in the final analytical and address data that would serve to validate the association.

In another embodiment, the invention provides for methods for registering an analytical image (e.g. an image from an assay to detect target analytes, rather than a decoding image) of a microsphere array comprising providing a hybridization intensity image as outlined herein. The sample is added to decode the microsphere array and a hybridization intensity image is acquired from the array. For reasons not fully understood, it turns out that certain target/capture probe pairs fluoresce at different intensities, despite the general equivalence of the number of fluorophores and the assay conditions across many beads. That is, while highly multiplexed systems are used, with all target/capture probe pairs being treated essentially identically, the signal intensities of certain target sequence/capture probe (e.g. adapter sequences) pairs are different. Without being bound by theory, this may be due to differences in secondary or tertiary structure of the pairs, leading to altered hydrophobicity/hydrophilicity of the environment of the fluorophores and a resulting alteration in signal intensity. Thus, these sets of "bright" beads, which consistently give higher signal intensities in an analytical image, are used as a set of fiducial beads, allowing the construction of a "registration grid".

Thus, depending on the particular assay, bright beads are distributed throughout the array and can be used as fiducials. A registration grid is computed from the decoding data obtained from a decoding step. A "registration grid" is essentially a map that marks the relative location of each bead of each bead type. The objective is to correctly overlay the registration grid on to the hybridization intensity image, so that the intensity at each grid location is the intensity of the bead (of a particular bead type) believed to be at that location (according to decoding). The registration grid is aligned so that the identity of the location of each core of each microsphere within the array is ascertained. Once the correct position of the grid is obtained, each core is assigned a number so that the correct placement of the grid can be made for further sequential images.

When considering only the brightest bead type, the average intensity of the beads of the brightest bead type is maximal if the grid is at the correct position (if the grid is not at the right position, none of the bead types will have all its beads at one of the brightest spots). The registration grid will read the intensities of the underlying image at those places and compute an average intensity for each bead type of the array. One of the bead types will be the brightest. For every position of the grid (with respect to the underlying analytical image), a different bead type will be the brightest. None of the maximum intensities will be as bright as the intensity of the brightest bead type when the grid is positioned correctly be cause the probability that by accident all bead locations of a bead type fall on one of the brightest spots on the image is very small.

In a preferred embodiment 4-5 bright bead types are distributed throughout the array to serve as fiducials. By "bright bead" or "brightest bead type" herein is meant any bead type whose intrinsic signal intensity is higher than any other beads within the same array after hybridization between target and attached molecules of the microspheres of an array have taken place, forming a hybridization complex. In a preferred embodiment, at least 0.1% of the brightest bead types will serve as fiducials, more preferably at least 1% of the brightest bead types within an array will serve as fiducials, even more preferably at least 2% and most preferably at least 3% of the brightest bead types will serve as fiducials. Intrinsic signal intensity can be affected by many variables, such as the local assay environment, including base composition of nucleic acid, where the hybridization complex comprises DNA or RNA; amino acid composition where the hybridization complex comprises proteins; salt concentrations of buffers; pH of solutions used; and secondary and tertiary structures of the target analytes and thus the environment of the fluorophores. In a preferred embodiment a single bright bead type is used. In a further preferred embodiment, at least 3 bright bead types (e.g. the three brightest bead types), more preferably at least 4 bright bead types, and most preferably at least 5 bright bead types are used as reference points. However, as will be appreciated by those in the art, "dim" bead types can also be used. That is, just as some target/capture probe pairs are inherent bright, some are inherent "dim", that is, have a lower inherent fluorescent intensity. Thus, combinations of the "brightest" and the "dimmest" can be used, with again, at least 1 to 5 bead types being used.

In addition, it is possible to alter the signal intensities on purpose, to create brighter or dimmer bead type sets. For example, during the amplification process, primers for certain sequences can include more or less fluorophores than other amplification reactions.

The actual number of beads used in the bead type set for calculation of the bright beads and the generation of the registration grid can vary, with anywhere from 3 (the minimum to ensure spatial positioning) to the maximum number of that bead type. For example, in assays that utilize 50,000 with 2,000 targets, there is a general 40× redundancy, so all 40 beads of that bead type could be used. Alternatively, less than the entire set can be used.

The invention provides for methods of grid placement and correct analytical image registration through the use of tracking the intensities of the brightest bead types during alignment of a virtual grid. Once the hybridization intensity image is obtained at least one bright bead serves as a fiducial for correct grid placement. Computer methods are used to overlay a constructed matrix or grid of putative bead locations onto the image, to ascertain the location of each core of each microsphere within the array. During alignment of the grid, the percentage of the sum of all the brightest bead types at any correct position will be at a maximum over the sum of the brightest bead type intensities at any incorrect position. At the correct registration position the percentage of the brightest bead type intensity at correct position over brightest bead type intensity at any incorrect position should be >10. Once the correct position of the grid is obtained, each core is assigned a number so that the correct placement of the grid can be made for further sequential images.

The ratio of the average cv at the correct registration position over average cv of at least 20 incorrect registration positions should be <0.5, more preferably <0.4 and most preferably <0.3. By "average cv" as used herein is meant the normalized standard deviation of the number of the brightest beads of all bead types.

By "analytical image" or "hybridization intensity image" as used herein is meant an image of signal intensities of a population of microspheres within an array obtained after the array is contacted with target analytes. Hybridization takes place between the chemistries attached to the microspheres and molecules within the sample, molecules such as oligonucleotides and proteins, with the former being preferred. In a preferred embodiment signal intensifies refer to fluorescent intensities when fluorescent labels are used, but other labels can also be used in the methods of this invention as would be appreciate by one skilled n the art, such as isotopic, magnetic, or other optically active labels. When fluorescent labels are used, and after illumination of the hybridization complex has taken place, signal intensities of all beads produces a particular pattern of fluorescent intensities amongst the microspheres of the array, this pattern produces an image which is referred to herein as an "analytical image" or "hybridization intensity image".

In a preferred embodiment, the fiducial is a defined edge or edges of the substrate. As will be appreciated by those in the art, this may be done in a variety of ways. In one embodiment, a coating or sheath of fiducial material, such as highly fluorescent glass, is incorporated into the array composition. The fiducial material can have any number of physical characteristics to allow registration; for example, a "stripe" of fiducial material may have notches, dark impurities, or other identifying features along its length. Alternatively, the fiducial material is placed in discrete spots or discrete shapes; basically, any orientation that allows translation, rotation, enlargement or reduction of images to be detected can be used.

In one embodiment, when an edge is used as a fiducial, the image of the array is obtained and the edges are determined. The edges are then used to align subsequent images of the same array.

In a particularly preferred embodiment, the edges, which can be an interface between different portions of the fiber bundle, are determined following a morphological erosion-type crossing (e.g. 4 passes of cross 3×3 erosion) which removes the small feature size items, e.g. beads, from the image. That is, although not required in all embodiments, the image of the beads is removed. An edge detection algorithm (e.g. Sobel) is applied to the image to extract the boundaries. When the image of beads is not removed, the edge of the beads also is determined. The image thus obtained is used as a template image upon which other images are placed so that the images are aligned and can be compared. That is, images containing bead intensities, for example, are aligned with the template.

To align the images the cross point of two edges is found. For example, the non-template image is rotated around a pivot point or cross point until a line or fraction of a line is apparent. The image can then be shifted up or down to completely align the images.

Having aligned the images, the amount and direction of rotation an shift can be recorded and used on a data processing algorithm, for example FiberWorks, which uses the alignment data to align all images obtained for a particular array.

The use of array edges as fiducials provides several advantages over fiducial beads or fibers. Namely, the fiducial edge negates the requirement of preparing fiber bundles containing special fiducial fibers. This markedly reduces the expense and difficulty in preparing fiber bundles.

In addition, the use of a fiducial edge increases the signal to noise ratio of an image. That is, the use of a fiducial edge results in the ability to increase sensitivity of imaging. For example, fiducial fibers are frequently designed to have a higher intensity than the beads. A result of this is that the fiducial fibers diminish the maximum signal integration time. That is, because of the higher signal intensity of the fiducial, the integration time, which is the time in which the CCD collects an image, frequently is reduced to avoid saturation of the CCD array cell by the fiducial. Thus, to prevent saturation, integration time is diminished. As a result, signals obtained from the beads are reduced. Thus, by the use of at least one fiducial edge instead of fiducial fibers, the signal-to-noise ratio of a bead is increased. That is, the exposure or integration time is increased resulting in improved signals.

An additional advantage of using a fiducial edge is that alignment is independent of detector channels. That is, alignment does not depend on the detection of a particular signal (such as a color) from a fiducial fiber or bead. An example is illustrative. When a fiducial fiber or bead is used, detection of the signal from that fiducial is dependent on analyzing the data with a channel that corresponds with the fiducial signal. When multiple color channels are used for the detection of multiple signals, it is possible that the fiducial may not show up in a particular color channel or not appear sufficiently strong for alignment purposes. Accordingly, the use of a fiducial edge provides for alignment in all possible channels. That is, alignment is independent of the color channels used for detection of the array signals.

In addition, the use of a fiducial edge increases the precision of alignment. That is, because of the reduced diameter of a fiducial edge (generally 1-2 pixels) compared to the diameter of a fiducial fiber (generally about 17 pixels wide), the fiducial edge allows for alignment of images with the increased precision. Generally the precision is increased more than 2 fold; more particularly from 2 to 50 fold, or further, from 2 to 10 fold.

In a preferred embodiment, an exogenous fiducial is not used; rather, inherent characteristics of the array are used. That is, rather than incorporate a special feature into the array to serve as a fiducial, the inherent variability of the features of an array is used to create a sort of "fiducial template". In this embodiment, an image of the array is taken under conditions in which all the features are illuminated evenly and can be differentiated from one another. For example, the surface of the substrate can be illuminated with white light in such a way that all the features are illuminated evenly. This finds particular use when the substrate is a fiber optic bundle with etched wells, in that the illumination angle and intensity is chosen such that the light reflecting off the beads differs in intensity from the light reflecting off the cladding and spacer material. Preferred embodiments utilize polarized light or light impinging at various angles. Alternatively, the surface of the array may be contacted with a fluorescent solution, allowing fluorescence to be collected equally by all the features.

In a preferred embodiment, particularly when the substrate includes fiber bundles, a preferred fiducial template technique is used. As outlined herein, the present invention relies on sequential imaging of extremely high density arrays and thus the registration of the images is crucial. One potential problem is that sequential images may be shifted, rotated, enlarged or contracted relative to other images. The challenge is to find the same microsphere from image to image. Accordingly, the present invention provides fiducial template techniques that can allow correct alignment.

Thus, in a preferred embodiment, the present invention provides computer methods to overlay a constructed matrix or grid of putative bead locations onto the image, to ascertain the correct placement of the image. In this embodiment, the software constructs a grid that corresponds to the structures of the fiber bundles (or other pattern of beads). In general, hexagonal fiber bundles are constructed of hexagonal "mini-bundles" that are placed together, as is generally depicted in FIG. 6. While the following description is directed to fiber bundle arrays, one of skill in the art will appreciate that these methodologies are useful with microsphere arrays with any substrate.

The process is generally outlined as follows. An artificial "sub-bundle", comprising a number of minibundles, is chosen. Generally, the sub-bundle includes the minibundle in the center of the array, although this is not required. Preferably, the sub-bundle is a symmetric sub-bundle as depicted in FIG. 6A. However, linear or non-symmetric sub-bundles may also be chosen. In general, the sub-bundle includes at least three minibundles, with from about 3 to about 25 being preferred, and 10-20 being particularly preferred. FIG. 6 depicts a 19 minibundle sub-bundle.

An image is acquired, usually using white or laser light. The virtual grid is applied to the image, and then the image is analyzed by starting at the center. The first minibundle is positioned around the center, and the other minibundles of the sub-bundle are tiled around it, and then the remaining minibundles of the array are placed or tiled as well, until the edges are reached. The software then scans along the edges, looking at the cores or beads. Correct positioning is evaluated by counting the number of detectable cores on the outmost row of the projected grid and comparing it with the number of detectable cores on the outermost row when the grid is shifted in one or more of each of the six directions of the hexagon. That is, edge cores should not have additional neighboring cores; the identification of external neighboring cores on a putative edge core requires the grid to be repositioned on the image in one or more directions. The grid is repositioned in core to core jumps. Once the correct placement is reached, each minibundle is assigned a number, and each core within each minibundle is assigned a number, as is generally depicted in FIG. 6B. Thus, comparisons between images are facilitated.

In a preferred embodiment, the grid is placed by reference not to the edges, but by reference to particular beads. Thus, for example, the redundancy of the arrays of the invention means that there are sets of beads, scattered throughout the array, that can serve as the reference points for alignment of the grid. Reference can be made to bright beads or dim beads, etc. For example, in this embodiment, the grid can be placed, the cores tiled, and then checked to see if the bright beads are where they are supposed to be. If not, as above, the grid can be repositioned and reanalyzed. In addition, in this embodiment, fiducial beads or cores can be used for grid placement.

Thus, the grid allows the correct placement of each core in the array, even if image acquisition results in some shifting or rotation of the images. It further allows data acquisition and placement even if faulty images are acquired, e.g. if part of the array is damaged for some reason.

In a preferred embodiment, the mapping between core indices and grid coordinates is done as follows. The Sector/Radius/Tangent address of the minibundles (sometimes referred to herein as HexGrids) with fiducial beads is determined and the fiducial beads are positioned within the HexGrid. The following example is the determination of which address on the grid contains core (bead) 22341, using minibundles comprising 91 cores.

Find the mini_bundle_number: MG=(22341 div 91)+1=246

$core_{13}$ number (inside minibundle) CN=(22341 mod 91)+1=47

Quadratic equation: $ax^2 + bx + c = 0$ solution x1,2=(-b ±sqrt[$b^2$ -4ac])/(2a)

MBO (RNO*(RN0+1))/2 (number of minibundles in one $tetra_{13}$ grid(sector), RNO)=row number MB=6*(RNO*(RNO+1))/2) (number of minibundles in all $tetra_{13}$ grids (sectors))

<=>RNO^2+RNO−(2*(MB/6))=0

==>RNO=(−1+sqrt(1+(8*(MB/6))))/2 row_number (radius): R=1+floor(RNO)

remainder minibundles: Re=(MB−1)−(6*(((R−1)*R)/2)) (subtract all minibundles underneath)

tetra_grid (sector): S=(Re div RNO)+1 position (tangent) T=Re−((S−1)*R); (RN of center minibundle is 0)

Solution: (Sector S, Row R, Tangent T); same formula for core_number

Formula that maps core address to minibundle index:

$$MB=(6*(((r-1)*r)/2))+((s-1)*r)+t+1$$

where MB=minbundle, s=sector, r=radius, and t=tangent

This grid/tiling procedure provides a number of benefits. Accurate, robust registration of the images can be done, and it is efficient and accurate in the detection of orientation, scale and core locations near the center of the bundle through grid fitting. The system is robust enough to allow the handling of background images, truncated images, and arrays without exogenous fiducials. In addition, accurate sub-pixel core centering can be done, as the grid averages out positioning errors of individual cores. The system adapts to non-linear local and global distortions and provides consistent (grid-based) core indexing. Furthermore, the grid allows the identification of neighboring cores/beads allows bleed-through analysis. In addition, the system can be used either for decoding or for analytical image acquisition and analysis.

Additionally, the methods outlined below relating to "bleed-through" preprocessing may also be used as a type of endogenous fiducial. As outlined below, a preprocessing step allows the determination of which wells contain beads, based on the presence or absence of characteristic dye signals; that is, if a signal characteristic of any of the dyes on the array (i.e. a "bleed through signature"), is not present for a particular array location, then the site on the array is determined to be without a bead. This information, which can be done for each sequential assay, can be used as a fiducial template as well.

In a preferred embodiment, the invention provides the use of an image produced by a randomly ordered array to identify and/or label the array. When forming a random array, many, but not all, of the microwells on an array are filled with microspheres. The filled versus unfilled sites on the array are randomized; thus, an image or a composite of images of an array that details the filled from unfilled locations on the array serves as a unique identifier of the array. Thus, the image of a particular array is statistically different and distinct from an image or a composite of images of another array even though the different arrays have functional equivalence. By "statistically different" is meant that although there is a theoretical probability that two arrays may be similar, the probability is so small as to be insignificant or unimportant.

In one embodiment, the arrays have at least one subpopulation of microspheres. The pattern on the array created by the random assembly of microspheres on the array serves to identify the particular array. The image of the array registers the location of each bead such that composite images taken from the array can be compared directly. For example, an image produced by an array after exposure to a first substance can be directly compared with the same array exposed to a second substance. Alternatively, a single population of microspheres can be analyzed by multiple wavelengths and directly compared.

In another embodiment, these arrays have two or more subpopulations represented in each array. Because the arrays are assembled randomly, the individual locations of beads representing each subpopulation are randomized. Thus, an image or a composite of images that registers the location of each bead in a particular subpopulation will be statistically different from an image or composite of images of another array even though the different arrays have functional equivalence. Likewise, the image or composite of images for another subpopulation within the same array will be statistically different from an image or composite of images of another array.

In addition, the number of beads of each subpopulation that actually populate a given array can vary. The specific number of beads within a subpopulation on an array is approximated by a Poisson distribution. The variation in number of beads representing a subpopulation adds another dimension to identifying individual arrays.

The recognition that functionally equivalent arrays result in different images affords one the possibility of using that difference to "fingerprint" each array. Essentially, each random array has a built in method for identifying and tracking that array.

Thus, the invention facilitates the use of innate features within a random array to identify and track a specific array. The ability to identify and track a specific array has important functionality ain quality control monitoring, inventory monitoring, performance monitoring and use monitoring. For example, the ability to identify an array will allow one to determine when it is used and whether it is reused.

In a preferred embodiment, the template image is used to define a "grid" which is placed upon the data images. The use of a template image to define the location of features is optional, although currently preferred. Using standard image processing software such as IMAGE-PRO® software (Media Cybernetics) a template is built based on this grid. This type of software allows the user to create simultaneous software segments to calculate the mean feature intensity over a region of interest using a simple, one step segmentation function. This software-based fiducial template can then be mapped onto each data image in the assay protocol to allow data collection for each region for each data image. See for example U.S. Pat. No. 5,768,412. This allows the location of each array feature to be defined.

In a preferred embodiment the method employs two-dimensional Fourier Transformation in order to find the invariant features of a fiber bundle. Due to the hexagonal architecture of fibers in a fiber bundle (not the shape of the bundle's envelope), there are three major directional periodic signals. Assuming the fiber bundle of FIG. 7, the three major directions of periodic signals are in the following directions: 0 degrees, 60 degrees and −60 degrees.

Fourier Transform will project these repetitive cores into single dots in the Fourier plane. Therefore, there would be one dot for the repetitive signal along the 0 degree angle. Due to the symmetry of the Fourier Transform, the mirror image of this point will also be present in the abs (Fourier(Image)).

The cores along the 60-degree axis will result in two dots on the Fourier Plane (along the 60-degree axis). Similarly, the cores along the −60-degree axis will result in two dots on the Fourier Plane (along the 60-degree axis). Therefore, the whole pattern of a fiber bundle is projected onto a single hexagon (only 6 points). The radius of this hexagon is equal to 2*pi/T where T is the pitch of the cores in the fiber bundle.

As the image rotates, so will the hexagon in the Fourier Plane. The degree of rotation of the Fourier domain hexagon is the same as the degree of rotation of the original image (with respect to the template image), Therefore, one can detect the rotation angle of one image from the template image, by gauging the angle of rotation of the resultant hexagon in the Fourier Plane.

The amount of scaling can also be found from the Fourier Transformed images. As was stated above, the pitch in the Fourier Plane is inversely proportional to the pitch in the original (space) plane. Therefore, as the scale of the image is increased, the size of the hexagon (in the Fourier Plane) will be reduced proportionally.

One may employ the method of least squares for scaling and rotating the resultant hexagons (in the Fourier Plane). Once the rotation and scale have been applied, the only other needed operation would be a shift in the x and y directions. One can use the phase shift information in the Fourier Transformed image to align cores. Then, one can use the other available methods to do the final shifts in x and y directions.

FIGS. 8A and 8B shows additional examples. Of note the method of this invention is effective, even for dim background and out-of-focus images. The reason for the strength of this method is that the signal power in the space domain is preserved after the transformation into the Fourier domain. In the space domain, the signal power is distributed on the whole fiber bundle. However, in the Fourier domain, all the signal power is concentrated on the 6 vertices of the hexagon (and also the center).

Major advantages of this invention include finding the amount of rotation and scale between the two images. Having the complete image is not necessary. One can use cropped pieces (from different parts) of the two images. Some windowing function (such as Hamming Window, Hanning Window, Blackman Window, etc.) can help reduce the ringing effect due to the sharp edges. The result would be cleaner background in the Fourier image. This idea can also be used for auto-focusing problem. FIG. 8 demonstrates that as the images focus, the hexagon in the Fourier Domain becomes more visible.

In additional preferred embodiment radon transformation is used for image registration. FIGS. 9 and 10 show the main embodiment of this invention. First the original image is read, and the internal cores are disintegrated, for example, using Closing morphological operations. Then an edge detection method is used (Sabel, for example), to define the boundary of the beads. Radon Transformation is then performed. The notches (6 high intensity dots) identify the scale, rotation and the translation for the image. These 6 parameters can be used to perform image registration completely.

Without being bound by theory, it is thought that points along a straight line (in the original space) will end up in intersecting sinusoids in the Radon space. The more the number of points in the original space, the more pronounced will the intensity of the intersecting sinusoids be in the Radon space. The reason Step 2 is needed is to remove internal beads from the computations, as beads make straight lines too. The only straight lines of interest for this are the ones in the boundary of the beads, and not the internal beads.

Hough Transform can also be used instead of Radon Transform. However, Hough Transform has the limitation of ambiguity for the points on vertical lines. Thus, while Radon Transform may be more robust because it does not have this limitation, Hough Transform is an alternative method.

Once the microspheres comprising the candidate agents and the unique tags are generated, they are added to the substrate to form an array. In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for attachment of the beads. This may be done in a variety of buffers, including aqueous and organic solvents, and mixtures. The solvent can evaporate, and excess beads removed.

It should be noted that not all sites of an array may comprise a bead; that is, there may be some sites on the substrate surface which are empty. In addition, there may be some sites that contain more than one bead, although this is not preferred.

It should additionally be noted that in some cases, empty sites can serve as fiducials. That is, consistently "dark" sites can also be used as fiducials. This finds particular use when the filling efficiencies of the array are high; that is, when most sites contain a bead. In addition, the dark sites also can be used to "fingerprint" the array as described above. That is, the image of light and dark sites serves to define or identify a particular array. This image also serves to register the array for comparison purposes.

In some embodiments, for example when chemical attachment is done, it is possible to attach the beads in a non-random or ordered way. For example, using photoactivitable attachment linkers or photoactivitable adhesives or masks, selected sites on the array may be sequentially rendered suitable for attachment, such that defined populations of beads are laid down.

The arrays of the present invention are constructed such that information about the identity of the candidate agent is built into the array, such that the random deposition of the beads in the fiber wells can be "decoded" to allow identification of the candidate agent at all positions. This may be done in a variety of ways, and either before, during or after the use of the array to detect target molecules.

Thus, after the array is made, it is "decoded" in order to identify the location of one or more of the bioactive agents, i.e. each subpopulation of beads, on the substrate surface. In general, both decoding and the experimental assay to determine the presence or absence of a target analyte, both of which are described below, requires the comparison of sequential data images to determine the differences between two data images. In general, this is done by taking a first or initial data image, using the fiducial to create a registered first data image, subjecting the array to decoding conditions and taking a second data image. The same fiducial is used to create a registered second data image, and then the two registered images can be compared. In this context, a "data image" includes a primary data image or a reduction of the image; for example, the image may be reduced to a set of X-Y coordinates with corresponding intensity values.

In a preferred embodiment, this is done using a computer system comprising a processor and a computer readable memory. The computer readable memory comprises an acquisition module that comprises computer code that can receive a data image from a random array and a registration module comprising computer code that can register the data image using at least one fiducial, including a fiducial template, to generate a registered data image. This registered data image can then be stored in a storage module as needed. This same computer code, or different code, if required, can be used to receive additional data images and generate additional registered data images, which also can be stored. The computer readable memory further comprises a comparison module comprising computer code that can compare the registered data images to determine the differences between them, to allow both decoding of the array and target analyte detection. That is, when decoding is done, the comparison of at least two registered data images allows the identification of the location of at least two unique bioactive agents on the array.

As a preliminary matter, prior to decoding, a filtering step or preprocessing step is performed (although in some embodiments this step is performed during or after decoding). That is, in some embodiments, filtering or preprocessing is performed on the array. In one embodiment, the preprocessing serves to identify the array elements that contain no beads or contain faulty beads. That is, as described in detail below, preprocessing identifies the array locations that do not contain a detectable signal or contain a signal that is not similar to a reference signal or signals. These locations are defined as containing no beads or containing faulty beads and thus can be dropped from the analysis, giving a higher confidence level for the remaining sites.

In an alternative embodiment, filtering or preprocessing serves to categorize the beads into subpopulations; i.e. beads with similar characteristics, such as color, may form a subpopulation. The subpopulations may be used for additional data processing such as signal summing, statistical analyses or comparison. This may also serve to allow outliers within a subpopulation to be identified and discarded, resulting in higher confidence levels, higher signals and lower background.

Generally, the preprocessing is performed by analyzing or detecting a signal obtained from at least one of the array locations and determining whether the array location contains a bead. If the array location does contain a bead with a detectable signal, the bead may be further categorized into subpopulations containing similar signals, although this is not required. If it is determined that the assay location does not contain a bead, the assay location may be disregarded during additional analyses.

In one embodiment, the signal obtained from array location is an optical signature of the bead. That is, as described herein, beads or microspheres can be labeled directly or indirectly with dyes or fluorophores. Any of the optical signatures as described herein find use with preprocessing of the array image.

In a preferred embodiment, the optical signature is derived from the bleed-through information that is obtained from an image. By "bleed-through" is meant the data obtained from a signal as recorded from multiple channels. That is, while in an ideal situation, each dye is highly specific and only gives a signal at a particular wavelength, the use of fluorescence in general and multiple "colors" in particular often results in a "bleed through" from one wavelength channel to another. Thus any particular signal give a peak measurement at its specific wavelength, but then gives an additional signal at other wavelengths. Thus, any signal is analyzed by a plurality of measures or channels and the results obtained by the different measures or channels can contribute to a total signal or signature: a characteristic dye will give not only a characteristic signal, but also a characteristic bleed-through signature; this may be used as a further confidence measure.

An example is illustrative. Generally, when viewing an image of a particular color, the ideal output corresponds to a signal that corresponds precisely with the color being viewed. However, due to the bleed-through into different color channels, for example, the response of various color channels is not independent. That is, although only a particular signal or color is being monitored with a particular channel, the absorbance spectrum i.e. band-width, for that color extends beyond or is generally larger than the channel used to monitor the particular signal; the band-width frequently overlaps into other channels. The resulting bleed-through creates a signature, for example, when the image is viewed across a variety of channels (see FIG. 3). As exemplified in FIG. 3, the output maximum of C1 "bleeds-through" resulting in signals C2, C3 and C4. Thus, the output of a single signal when viewed through multiple channels results in a "bleed-through" signature of that signal.

Generally, the "bleed-through" signature is generated as follows. The intensity of each image, for example, a bead or microsphere, in various channels is obtained and viewed as a vector in N-dimensional space (where N is the number of images in that stage). The angle between this vector and the vectors of the theoretical bleed-through, which will vary depending on the optics, is made based on the inner product of the vectors. The angle, which defines the similarity measure, is characterized by the following formula:

$$\theta = \cos^{-1} \frac{\vec{A} \cdot \vec{B}}{|\vec{A}| \simeq \Box \vec{B}|}$$

Once the similarity measure, i.e. the angle between the vectors, has been calculated, a funnel is defined (FIG. 4) that establishes the threshold for the similarity between the experimentally determined vector and the theoretically determined vector. The "funnel", therefore, defines the area within which other signatures must fall to be considered similar to the original optical signature.

In addition, similarity measures for a plurality of optical signatures can be obtained. Results from the analysis of any particular image or bead, are compared to the plurality of reference similarity measures to determine if the image or bead is similar to a pre-determined or reference optical signature. That is, the signature of a given image is analyzed to determine if the signal falls within one of the funnels that define the similarity measures for the plurality of reference optical signatures. If it does, the bead data is retained; if it does not, it may be discarded.

Thus, although the "bleed-through" effect has generally been considered an undesirable effect, the present invention provides for using this effect in analyzing signals obtained from the array.

The similarity measure finds use in variety of ways with the present invention. In one embodiment, the similarity measure of each image or bead is determined and compared with the similarity measure of the reference image and the theoretical signal. If the angle of the similarity measure is equal to or less than that of the similarity measure between the reference image and the theoretical image, the signal of the bead is similar to that of the reference bead. That is, the similarity measure of an assay location is examined to determine if it falls within the funnel obtained from the similarity measure between the reference image and the theoretical image. If the signal of the assay location falls within the funnel, the signal from the bead is similar to that of the reference.

In addition, the similarity measure of an assay location can be compared with a plurality of reference similarity measures obtained for different signals. As described above, if the angle of the similarity measure is equal to or less than that of the similarity measure between one of the reference images and any of the theoretical images, the signal of the bead is similar to that of one of the reference beads. That is, if the angle of the similarity measure falls within any of the funnels obtained from the similarity measure between a reference image and a theoretical image, the signal from the assay location is similar to the reference.

As described herein, identification of the optical signature of a particular bead serves, in some embodiments, to identify the bioactive agent on the bead. In addition, identification of assay locations that contain signals that are similar to pre-determined or reference signals identifies that assay location as containing a bead. It follows, therefore, that assay locations that do not contain signals that are similar to pre-determined or reference signals identifies those assay locations as either not containing beads, or containing defective beads. That is, if the angle of the similarity measure obtained from the signal at an assay location is larger than the reference similarity measure, i.e. if the similarity measure does not fall within the funnel, the signal is not similar to the reference bead and therefore the assay location can be diagnosed as not containing a bead or containing a defective bead. Without being bound by theory, it is thought that an empty assay location does not have a large intensity, and/or its signature is not likely to map into one of the reference signatures (FIG. 5).

Accordingly, in one embodiment pre-processing as described above finds use in determining the presence or absence of a bead on an assay location. That is, as described above, a similarity measure is obtained for an assay location on an array and compared to the threshold similarity measure for each reference color. If the angle of the similarity measure is larger than any of the reference similarity measures, the assay location is considered to not contain a bead or contain a defective bead and its data is either ignored or not calculated.

In an alternative embodiment, similarity measures find use in categorizing a signal obtained from an assay location. That is, as described above, a similarity measure is obtained for an assay location on an array and compared to the threshold similarity measure for each reference color. If the angle of the similarity measure is less than any of the reference similarity measures, the signal obtained from that assay location is considered to have the same signal as that of the reference signal.

This method finds particular use when clustering beads for analysis and/or comparison. That is, in some embodiments it is useful to cluster beads with the same optical signatures. Those beads that are not similar are excluded from the cluster. The signal(s) from the clustered beads can then be analyzed by summing the signals or other statistical analyses. Signal summing and statistical analyses are more thoroughly described in U.S. Ser. Nos. 08/6944,850 and 09/287,573 and PCT/US98/21193 and PCT US00/09183, all of which are expressly incorporated herein by reference in their entirety.

Thus, using the systems described herein, a random array is decoded as is generally described in U.S. Ser. Nos. 60/090, 473, 09/189,543 and 09/344,526 and PCT/US99/14387, all of which are expressly incorporated herein by reference in their entirety. In a preferred embodiment, a selective decoding system is used. In this case, only those microspheres exhibiting a change in the optical signal as a result of the binding of a target analyte are decoded. This is commonly done when the number of "hits", i.e. the number of sites to decode, is generally low. That is, the array is first scanned under experimental conditions in the absence of the target analytes. The sample containing the target analytes is added, and only those locations exhibiting a change in the optical signal are decoded. For example, the beads at either the positive or negative signal locations may be either selectively tagged or released from the array (for example through the use of photocleavable linkers), and subsequently sorted or enriched in a fluorescence-activated cell sorter (FACS). That is, either all the negative beads are released, and then the positive beads are either released or analyzed in situ, or alternatively all the positives are released and analyzed. Alternatively, the labels may comprise halogenated aromatic compounds, and detection of the label is done using for example gas chromatography, chemical tags, isotopic tags mass spectral tags.

In a preferred embodiment, atomic force microscopy (AFM) is used to decode the array. In this embodiment, an AFM tip, comprising a DBL, is positioned at the site to be decoded, that comprises an IBL. The force of interaction between the IBL/DBL is measured using AFM. IN addition, since AFM has atomic resolution, a variety of other physical characteristics, including physical size and shape can be used for decoding. For example, different "shaped" molecules could be used as IBLs; in this embodiment, the AFM tip can comprise a DBL or just a moiety that can detect different surfaces. In addition, AFM could be used as "nanotweezers" to deliver or recover beads to and from specific locations on the array.

As will be appreciated by those in the art, this may also be done in systems where the array is not decoded; i.e. there need not ever be a correlation of bead composition with location. In this embodiment, the beads are loaded on the array, and the assay is run. The "positives", i.e. those beads displaying a change in the optical signal as is more fully outlined below, are then "marked" to distinguish or separate them from the "negative" beads. This can be done in several ways, preferably using fiber optic arrays. In a preferred embodiment, each bead contains a fluorescent dye. After the assay and the identification of the "positives" or "active beads", light is shown down either only the positive fibers or only the negative fibers, generally in the presence of a light-activated reagent (typically dissolved oxygen). In the former case, all the active beads are photobleached. Thus, upon non-selective release of all the beads with subsequent sorting, for example using a fluorescence activated cell sorter (FACS) machine, the non-fluorescent active beads can be sorted from the fluorescent negative beads. Alternatively, when light is shown down the negative fibers, all the negatives are non-fluorescent and the positives are fluorescent, and sorting can proceed. The characterization of the attached bioactive agent may be done directly, for example using mass spectroscopy.

Alternatively, the identification may occur through the use of identifier moieties ("IMs"), which are similar to IBLs but need not necessarily bind to DBLs. That is, rather than elucidate the structure of the bioactive agent directly, the composition of the IMs may serve as the identifier. Thus, for example, a specific combination of IMs can serve to code the bead, and be used to identify the agent on the bead upon release from the bead followed by subsequent analysis, for example using a gas chromatograph or mass spectroscope.

Alternatively, rather than having each bead contain a fluorescent dye, each bead comprises a non-fluorescent precursor to a fluorescent dye. For example, using photocleavable protecting groups, such as certain ortho-nitrobenzyl groups, on a fluorescent molecule, photoactivation of the fluorochrome can be done. After the assay, light is shown down again either the "positive" or the "negative" fibers, to distinguish these populations. The illuminated precursors are then chemically converted to a fluorescent dye. All the beads are then released from the array, with sorting, to form populations of fluorescent and non-fluorescent beads (either the positives and the negatives or vice versa).

In an alternate preferred embodiment, the sites of attachment of the beads (for example the wells) include a photopolymerizable reagent, or the photopolymerizable agent is added to the assembled array. After the test assay is run, light is shown down again either the "positive" or the "negative" fibers, to distinguish these populations. As a result of the irradiation, either all the positives or all the negatives are polymerized and trapped or bound to the sites, while the other population of beads can be released from the array.

In a preferred embodiment, the location of every bioactive agent is determined using decoder binding ligands (DBLs). As outlined above, DBLs are binding ligands that will either bind to identifier binding ligands, if present, or to the bioactive agents themselves, preferably when the bioactive agent is a nucleic acid or protein.

In a preferred embodiment, as outlined above, the DBL binds to the IBL.

In a preferred embodiment, the bioactive agents are single-stranded nucleic acids and the DBL is a substantially complementary single-stranded nucleic acid that binds (hybridizes) to the bioactive agent, termed a decoder probe herein. A decoder probe that is substantially complementary to each candidate probe is made and used to decode the array. In this embodiment, the candidate probes and the decoder probes should be of sufficient length (and the decoding step run under suitable conditions) to allow specificity; i.e. each candidate probe binds to its corresponding decoder probe with sufficient specificity to allow the distinction of each candidate probe.

In a preferred embodiment, the DBLs are either directly or indirectly labeled. By "labeled" herein is meant that a compound has at least one element, isotope or chemical compound attached to enable the detection of the compound. In general, labels fall into three classes: a) isotopic labels, which may be radioactive or heavy isotopes; b) magnetic, electrical, thermal; and c) colored or luminescent dyes; although labels include enzymes and particles such as magnetic particles as well. Preferred labels include luminescent labels. In a preferred embodiment, the DBL is directly labeled, that is, the DBL comprises a label. In an alternate embodiment, the DBL is indirectly labeled; that is, a labeling binding ligand (LBL) that will bind to the DBL is used. In this embodiment, the labeling binding ligand-DBL pair can be as described above for IBL-DBL pairs.

Accordingly, the identification of the location of the individual beads (or subpopulations of beads) is done using one or more decoding steps comprising a binding between the labeled DBL and either the IBL or the bioactive agent (i.e. a hybridization between the candidate probe and the decoder probe when the bioactive agent is a nucleic acid). After decoding, the DBLs can be removed and the array can be used; however, in some circumstances, for example when the DBL binds to an IBL and not to the bioactive agent, the removal of the DBL is not required (although it may be desirable in some circumstances). In addition, as outlined herein, decoding may be done either before the array is used to in an assay, during the assay, or after the assay.

In one embodiment, a single decoding step is done. In this embodiment, each DBL is labeled with a unique label, such that the number of unique tags is equal to or greater than the number of bioactive agents (although in some cases, "reuse" of the unique labels can be done, as described herein; similarly, minor variants of candidate probes can share the same decoder, if the variants are encoded in another dimension, i.e. in the bead size or label). For each bioactive agent or IBL, a DBL is made that will specifically bind to it and contains a unique tag, for example one or more fluorochromes. Thus, the identity of each DBL, both its composition (i.e. its sequence when it is a nucleic acid) and its label, is known. Then, by adding the DBLs to the array containing the bioactive agents under conditions which allow the formation of complexes (termed hybridization complexes when the components are nucleic acids) between the DBLs and either the bioactive agents or the IBLs, the location of each DBL can be elucidated. This allows the identification of the location of each bioactive agent; the random array has been decoded. The DBLs can then be removed, if necessary, and the target sample applied.

In a preferred embodiment, the number of unique labels is less than the number of unique bioactive agents, and thus a sequential series of decoding steps are used. To facilitate the discussion, this embodiment is explained for nucleic acids, although other types of bioactive agents and DBLs are useful as well. In this embodiment, decoder probes are divided into n sets for decoding. The number of sets corresponds to the number of unique tags. Each decoder probe is labeled in n separate reactions with n distinct tags. All the decoder probes share the same n tags. The decoder probes are pooled so that each pool contains only one of the n tag versions of each decoder, and no two decoder probes have the same sequence of tags across all the pools. The number of pools required for this to be true is determined by the number of decoder probes and the n. Hybridization of each pool to the array generates a signal at every address. The sequential hybridization of each pool in turn will generate a unique, sequence-specific code for each candidate probe. This identifies the candidate probe at each address in the array. For example, if four tags are used, then 4×n sequential hybridizations can ideally distinguish $4^n$ sequences, although in some cases more steps may be required. After the hybridization of each pool, the hybrids are denatured and the decoder probes removed, so that the probes are rendered single-stranded for the next hybridization (although it is also possible to hybridize limiting amounts of target so that the available probe is not saturated. Sequential hybridizations can be carried out and analyzed by subtracting pre-existing signal from the previous hybridization).

An example is illustrative. Assuming an array of 16 probe nucleic acids (numbers 1-16), and four unique tags (four different fluors, for example; labels A-D). Decoder probes 1-16 are made that correspond to the probes on the beads. The first step is to label decoder probes 1-4 with tag A, decoder probes 5-8 with tag B, decoder probes 9-12 with tag C, and decoder probes 13-16 with tag D. The probes are mixed and the pool is contacted with the array containing the beads with the attached candidate probes. The location of each tag (and thus each decoder and candidate probe pair) is then determined. The first set of decoder probes are then removed. A second set is added, but this time, decoder probes 1, 5, 9 and 13 are labeled with tag A, decoder probes 2, 6, 10 and 14 are labeled with tag B, decoder probes 3, 7, 11 and 15 are labeled with tag C, and decoder probes 4, 8, 12 and 16 are labeled with tag D. Thus, those beads that contained tag A in both decoding steps contain candidate probe 1; tag A in the first decoding step and tag B in the second decoding step contain candidate probe 2; tag A in the first decoding step and tag C in the second step contain candidate probe 3; etc. In one embodiment, the decoder probes are labeled in situ; that is, they need not be labeled prior to the decoding reaction. In this embodiment, the incoming decoder probe is shorter than the candidate probe, creating a 5' "overhang" on the decoding probe. The addition of labeled ddNTPs (each labeled with a unique tag) and a polymerase will allow the addition of the tags in a sequence specific manner, thus creating a sequence-specific pattern of signals. Similarly, other modifications can be done, including ligation, etc.

In addition, since the size of the array will be set by the number of unique decoding binding ligands, it is possible to "reuse" a set of unique DBLs to allow for a greater number of test sites. This may be done in several ways; for example, by using some subpopulations that comprise optical signatures. Similarly, the use of a positional coding scheme within an array; different sub-bundles may reuse the set of DBLs. Similarly, one embodiment utilizes bead size as a coding modality, thus allowing the reuse of the set of unique DBLs for each bead size. Alternatively, sequential partial loading of arrays with beads can also allow the reuse of DBLs. Furthermore, "code sharing" can occur as well.

In a preferred embodiment, the DBLs may be reused by having some subpopulations of beads comprise optical signatures. In a preferred embodiment, the optical signature is generally a mixture of reporter dyes, preferably fluorescent. By varying both the composition of the mixture (i.e. the ratio of one dye to another) and the concentration of the dye (leading to differences in signal intensity), matrices of unique optical signatures may be generated. This may be done by covalently attaching the dyes to the surface of the beads, or alternatively, by entrapping the dye within the bead. The dyes may be chromophores or phosphors but are preferably fluorescent dyes, which due to their strong signals provide a good signal-to-noise ratio for decoding. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, pyrene, Malacite green, stilbene, Lucifer Yellow, Cascade Blue™, Texas Red, and others described in the 6th Edition of the Molecular Probes Handbook by Richard P. Haugland, hereby expressly incorporated by reference.

In a preferred embodiment, the encoding can be accomplished in a ratio of at least two dyes, although more encoding dimensions may be added in the size of the beads, for example. In addition, the labels are distinguishable from one another; thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the bioactive agents, using functional groups on the surface of the beads. As will be appreciated by those in the art, these attachments are done to minimize the effect on the dye.

In a preferred embodiment, the dyes are non-covalently associated with the beads, generally by entrapping the dyes in the pores of the beads.

Additionally, encoding in the ratios of the two or more dyes, rather than single dye concentrations, is preferred since it provides insensitivity to the intensity of light used to interrogate the reporter dye's signature and detector sensitivity.

In a preferred embodiment, a spatial or positional coding system is done. In this embodiment, there are sub-bundles or subarrays (i.e. portions of the total array) that are utilized. By analogy with the telephone system, each subarray is an "area code", that can have the same tags (i.e. telephone numbers) of other subarrays, that are separated by virtue of the location of the subarray. Thus, for example, the same unique tags can be reused from bundle to bundle. Thus, the use of 50 unique tags in combination with 100 different subarrays can form an array of 5000 different bioactive agents. In this embodiment, it becomes important to be able to identify one bundle from another; in general, this is done either manually or through the use of marker beads, i.e. beads containing unique tags for each subarray.

In alternative embodiments, additional encoding parameters can be added, such as microsphere size. For example, the use of different size beads may also allow the reuse of sets of DBLs; that is, it is possible to use microspheres of different sizes to expand the encoding dimensions of the microspheres. Optical fiber arrays can be fabricated containing features with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres in the smaller wells until all size wells are then filled. In this manner, the same dye ratio could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

In a preferred embodiment, the coding and decoding is accomplished by sequential loading of the microspheres into the array. As outlined above for spatial coding, in this embodiment, the optical signatures can be "reused". In this embodiment, the library of microspheres each comprising a different bioactive agent (or the subpopulations each comprise a different bioactive agent), is divided into a plurality of sublibraries; for example, depending on the size of the desired array and the number of unique tags, 10 sublibraries each comprising roughly 10% of the total library may be made, with each sublibrary comprising roughly the same unique tags. Then, the first sublibrary is added to the fiber optic bundle comprising the wells, and the location of each bioactive agent is determined, generally through the use of DBLs. The second sublibrary is then added, and the location of each bioactive agent is again determined. The signal in this case will comprise the signal from the "first" DBL and the "second" DBL; by comparing the two matrices the location of each bead in each sublibrary can be determined. Similarly, adding the third, fourth, etc. sublibraries sequentially will allow the array to be filled.

In a preferred embodiment, codes can be "shared" in several ways. In a first embodiment, a single code (i.e. IBL/DBL pair) can be assigned to two or more agents if the target analytes different sufficiently in their binding strengths. For example, two nucleic acid probes used in an mRNA quantitation assay can share the same code if the ranges of their hybridization signal intensities do not overlap. This can occur, for example, when one of the target sequences is always present at a much higher concentration than the other. Alternatively, the two target sequences might always be present at a similar concentration, but differ in hybridization efficiency.

Alternatively, a single code can be assigned to multiple agents if the agents are functionally equivalent. For example, if a set of oligonucleotide probes are designed with the common purpose of detecting the presence of a particular gene, then the probes are functionally equivalent, even though they may differ in sequence. Similarly, if classes of analytes are desired, all probes for different members of a class such as kinases or G-protein coupled receptors could share a code. Similarly, an array of this type could be used to detect homologs of known genes. In this embodiment, each gene is represented by a heterologous set of probes, hybridizing to different regions of the gene (and therefore differing in sequence). The set of probes share a common code. If a homolog is present, it might hybridize to some but not all of the probes. The level of homology might be indicated by the fraction of probes hybridizing, as well as the average hybridization intensity. Similarly, multiple antibodies to the same protein could all share the same code.

Once made, the compositions of the invention find use in a number of applications. In a preferred embodiment, the compositions are used to probe a sample solution for the presence or absence of a target analyte, including the quantification of the amount of target analyte present. By "target analyte" or "analyte" or grammatical equivalents herein is meant any atom, molecule, ion, molecular ion, compound or particle to be either detected or evaluated for binding partners. As will be appreciated by those in the art, a large number of analytes may be used in the present invention; basically, any target analyte can be used which binds a bioactive agent or for which a binding partner (i.e. drug candidate) is sought.

Suitable analytes include organic and inorganic molecules, including biomolecules. When detection of a target analyte is done, suitable target analytes include, but are not limited to, an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, nucleic acids, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are nucleic acids and proteins.

In a preferred embodiment, the target analyte is a protein. As will be appreciated by those in the art, there are a large number of possible proteinaceous target analytes that may be detected or evaluated for binding partners using the present invention. Suitable protein target analytes include, but are not limited to, (1) immunoglobulins; (2) enzymes (and other proteins); (3) hormones and cytokines (many of which serve as ligands for cellular receptors); and (4) other proteins.

In a preferred embodiment, the target analyte is a nucleic acid. These assays find use in a wide variety of applications.

In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, cytochrome p450s or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, chlamydia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella, Campylobacter, Vibrio cholerae, Leishmania*, enterotoxic strains of *E.*

*coli*, and Legionnaire's disease bacteria. Similarly, bioremediation strategies may be evaluated using the compositions of the invention.

In a further embodiment, the probes are used for forensic "DNA fingerprinting" to match crime-scene DNA against samples taken from victims and suspects.

In an additional embodiment, the probes in an array are used for sequencing by hybridization.

The present invention also finds use as a methodology for the detection of mutations or mismatches in target nucleic acid sequences. For example, recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants. There are a number of well known polymorphisms that cause clinically important phenotypes; for example, the apoE2/3/4 variants are associated with different relative risk of Alzheimer's and other diseases (see Cordor et al., Science 261 (1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33-39 (1998). The compositions of the present invention may easily be substituted for the arrays of the prior art.

In a preferred embodiment, the compositions of the invention are used to screen bioactive agents to find an agent that will bind, and preferably modify the function of, a target molecule. As above, a wide variety of different assay formats may be run, as will be appreciated by those in the art. Generally, the target analyte for which a binding partner is desired is labeled; binding of the target analyte by the bioactive agent results in the recruitment of the label to the bead, with subsequent detection.

In a preferred embodiment, the binding of the bioactive agent and the target analyte is specific; that is, the bioactive agent specifically binds to the target analyte. By "specifically bind" herein is meant that the agent binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding, although in some embodiments, wash steps are not desired; i.e. for detecting low affinity binding partners. In some embodiments, for example in the detection of certain biomolecules, the dissociation constants of the analyte to the binding ligand will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

Generally, a sample containing a target analyte (whether for detection of the target analyte or screening for binding partners of the target analyte) is added to the array, under conditions suitable for binding of the target analyte to at least one of the bioactive agents, i.e. generally physiological conditions. The presence or absence of the target analyte is then detected. As will be appreciated by those in the art, this may be done in a variety of ways, generally through the use of a change in an optical signal. This change can occur via many different mechanisms. A few examples include the binding of a dye-tagged analyte to the bead, the production of a dye species on or near the beads, the destruction of an existing dye species, a change in the optical signature upon analyte interaction with dye on bead, or any other optical interrogatable event.

In a preferred embodiment, the change in optical signal occurs as a result of the binding of a target analyte that is labeled, either directly or indirectly, with a detectable label, preferably an optical label such as a fluorochrome. Thus, for example, when a proteinaceous target analyte is used, it may be either directly labeled with a fluor, or indirectly, for example through the use of a labeled antibody. Similarly, nucleic acids are easily labeled with fluorophore, for example during PCR amplification as is known in the art. Alternatively, upon binding of the target sequences, a hybridization indicator may be used as the label. Hybridization indicators preferentially associate with double stranded nucleic acid, usually reversibly. Hybridization indicators include intercalators and minor and/or major groove binding moieties. In a preferred embodiment, intercalators may be used; since intercalation generally only occurs in the presence of double stranded nucleic acid, only in the presence of target hybridization will the label light up. Thus, upon binding of the target analyte to a bioactive agent, there is a new optical signal generated at that site, which then may be detected.

Alternatively, in some cases, as discussed above, the target analyte such as an enzyme generates a species that is either directly or indirectly optical detectable.

Furthermore, in some embodiments, a change in the optical signature may be the basis of the optical signal. For example, the interaction of some chemical target analytes with some fluorescent dyes on the beads may alter the optical signature, thus generating a different optical signal.

As will be appreciated by those in the art, in some embodiments, the presence or absence of the target analyte may be done using changes in other optical or non-optical signals, including, but not limited to, surface enhanced Raman spectroscopy, surface plasmon resonance, radioactivity, etc.

Again, as outlined above for decoding, the assay for the presence or absence of a target analyte utilizes sequential processing of data images using a computer system. Thus, in a preferred embodiment, a first data image of a random array is acquired using an acquisition module of the computer system. This initial data image may be decoded, i.e. the location of some or all of the bioactive agents may be known, or decoding may occur either during or after the assay. A registration module of the computer system is used to create a registered first data image, using either an exogeneous fiducial or a fiducial template generated by acquiring a template data image as outlined herein, for example by evening illuminating the array. The sample is then added to the array, and a second data image is acquired using the acquisition module. The fiducial and registration module are then used to create a registered second data image. A comparison module of the computer system is then used to compare the registered data images to determine the presence or absence of said target analyte.

The assays may be run under a variety of experimental conditions, as will be appreciated by those in the art. A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

In a preferred embodiment, two-color competitive hybridization assays are run. These assays can be based on traditional sandwich assays. The beads contain a capture sequence located on one side (upstream or downstream) of the SNP, to capture the target sequence. Two SNP allele-specific probes, each labeled with a different fluorophore, are hybridized to the target sequence. The genotype can be obtained from a ratio of the two signals, with the correct sequence generally exhibiting better binding. This has an advantage in that the target sequence itself need not be labeled. In addition, since the probes are competing, this means that the conditions for binding need not be optimized. Under conditions where a mismatched probe would be stably bound, a matched probe can still displace it. Therefore the competitive assay can provide better discrimination under those conditions. Because many assays are carried out in parallel, conditions cannot be optimized for every probe simultaneously. Therefore, a competitive assay system can be used to help compensate for non-optimal conditions for mismatch discrimination.

In a preferred embodiment, dideoxynucleotide chain-termination sequencing is done using the compositions of the invention. In this embodiment, a DNA polymerase is used to extend a primer using fluorescently labeled ddNTPs or other chain terminating nucleotides. The 3' end of the primer is located adjacent to the SNP site. In this way, the single base extension is complementary to the sequence at the SNP site. By using four different fluorophores, one for each base, the sequence of the SNP can be deduced by comparing the four base-specific signals. This may be done in several ways. In a first embodiment, the capture probe can be extended; in this approach, the probe must either be synthesized 5'-3' on the bead, or attached at the 5' end, to provide a free 3' end for polymerase extension. Alternatively, a sandwich type assay can be used; in this embodiment, the target is captured on the bead by a probe, then a primer is annealed and extended. Again, in the latter case, the target sequence need not be labeled. In addition, since sandwich assays require two specific interactions, this provides increased stringency which is particularly helpful for the analysis of complex samples.

In addition, primer extension is possible; extension of a primer bound to template in liquid phase is followed by capture of the extended primer on the array.

In addition, when the target analyte and the DBL both bind to the agent, it is also possible to do detection of non-labeled target analytes via competition of decoding.

In a preferred embodiment, the methods of the invention are useful in array quality control. Prior to this invention, no methods have been described that provide a positive test of the performance of every probe on every array. Decoding of the array not only provides this test, it also does so by making use of the data generated during the decoding process itself. Therefore, no additional experimental work is required. The invention requires only a set of data analysis algorithms that can be encoded in software.

The quality control procedure can identify a wide variety of systematic and random problems in an array. For example, random specks of dust or other contaminants might cause some sensors to give an incorrect signal-this can be detected during decoding. The omission of one or more agents from multiple arrays can also be detected. An advantage of this quality control procedure is that it can be implemented immediately prior to the assay itself, and is a true functional test of each individual sensor. Therefore any problems that might occur between array assembly and actual use can be detected. In applications where a very high level of confidence is required, and/or there is a significant chance of sensor failure during the experimental procedure, decoding and quality control can be conducted both before and after the actual sample analysis.

In a preferred embodiment, the arrays can be used to do reagent quality control. In many instances, biological macromolecules are used as reagents and must be quality controlled. For example, large sets of oligonucleotide probes may be provided as reagents. It is typically difficult to perform quality control on large numbers of different biological macromolecules. The approach described here can be used to do this by treating the reagents (formulated as the DBLs) as variable instead of the arrays.

In a preferred embodiment, the methods outlined herein are used in array calibration. For many applications, such as mRNA quantitation, it is desirable to have a signal that is a linear response to the concentration of the target analyte, or, alternatively, if non-linear, to determine a relationship between concentration and signal, so that the concentration of the target analyte can be estimated. Accordingly, the present invention provides methods of creating calibration curves in parallel for multiple beads in an array. The calibration curves can be created under conditions that simulate the complexity of the sample to be analyzed. Each curve can be constructed independently of the others (e.g. for a different range of concentrations), but at the same time as all the other curves for the array. Thus, in this embodiment, the sequential decoding scheme is implemented with different concentrations being used as the code "labels", rather than different fluorophores. In this way, signal as a response to concentration can be measured for each bead. This calibration can be carried out just prior to array use, so that every probe on every array is individually calibrated as needed.

In a preferred embodiment, the methods of the invention can be used in assay development as well. Thus, for example, the methods allow the identification of good and bad probes; as is understood by those in the art, some probes do not function well because they do not hybridize well, or because they cross-hybridize with more than one sequence. These problems are easily detected during decoding. The ability to rapidly assess probe performance has the potential to greatly reduce the time and expense of assay development.

Similarly, in a preferred embodiment, the methods of the invention are useful in quantitation in assay development. Major challenges of many assays is the ability to detect differences in analyte concentrations between samples, the ability to quantitate these differences, and to measure absolute concentrations of analytes, all in the presence of a complex mixture of related analytes. An example of this problem is the quantitation of a specific mRNA in the presence of total cellular mRNA. One approach that has been developed as a basis of mRNA quantitation makes use of a multiple match and mismatch probe pairs (Lockhart et al., 1996), hereby incorporated by reference in its entirety. While this approach is simple, it requires relatively large numbers of probes. In this approach, a quantitative response to concentration is obtained by averaging the signals from a set of different probes to the gene or sequence of interest. This is necessary because only some probes respond quantitatively, and it is not possible to predict these probes with certainty. In the absence of prior knowledge, only the average response of an appropriately chosen collection of probes is quantitative. However, in the present invention, that can be applied generally to nucleic acid based assays as well as other assays. In essence, the approach is to identify the probes that respond quantitatively in a particular assay, rather than average them with other probes. This is done using the array calibration scheme outlined above, in which concentration-based codes are used. Advantages of this approach include: fewer probes are needed; the accuracy of the measurement is less dependent on the number of probes used; and that the response of the sensors is known with a high level of certainty, since each and every sequence can be tested in an efficient manner. It is important to note that probes that perform well are selected empirically, which avoids the difficulties and uncertainties of predicting probe performance, particularly in complex sequence mixtures. In contrast, in experiments described to date with ordered arrays, relatively small numbers of sequences are checked by performing quantitative spiking experiments, in which a known mRNA is added to a mixture.

All references cited herein are incorporated by reference in their entirety.

We claim:

1. A method of registering an analytical image of a microsphere array comprising:
   a) providing a microsphere array, wherein said microsphere array comprises:
      i) a substrate with a surface comprising discrete sites; and
      ii) a population of microspheres comprising at least a first and a second subpopulation each comprising a bioactive agent, wherein said population of microspheres is distributed on said surface such that each of said discrete sites contain no more than 1 microsphere;
   b) decoding said microsphere array so that the location of each bioactive agent is elucidated;
   c) computing a registration grid based on known locations of said bioactive agents from information obtained from step (b);
   d) contacting said array with a sample comprising target analytes;
   e) acquiring a hybridization intensity image of said microsphere array, wherein said hybridization intensity image comprises a first bright bead type to serve as a fiducial;
   f) overlaying the registration grid onto said hybridization intensity image;
   g) determining an average intensity for the first bright bead type; and
   h) positioning the registration grid such that the average intensity of the first bright bead type is maximal, thereby registering the analytical image of the microsphere array.

2. A method according to claim 1, wherein said acquiring said hybridization intensity image comprises contacting said microsphere array with a sample forming a hybridization complex.

3. A method according to claim 1, wherein said hybridization intensity image comprises a population of microspheres randomly distributed on the surface of a substrate at discrete sites, wherein at least one site does not contain a microsphere, and wherein said site without a microsphere serves as a reference point for the alignment of said registration grid.

4. A method according to claim 1, wherein said substrate is a fiber optic bundle.

5. A method according to claim 4, wherein the step of aligning the registration grid to said hybridization intensity image comprises:
   (i) aligning said registration grid with hybridization intensity image features near a center area of the microsphere array;
   (ii) positioning a first minibundle around said center area;
   (iii) tiling other minibundles around said positioned first minibundle until an edge of said sub-bundle is reached;
   (iv) using a software program to scan along the edges of said sub-bundle;
   (v) correctly positioning said registration grid;
   (vi) assigning a first number to each minibundle; and
   (vii) assigning a second number to each core of each minibundle.

6. A method according to claim 1, wherein said microspheres are randomly distributed on the surface of said substrate.

7. A method according to claim 1, wherein said substrate is selected from the group consisting of glass and plastic.

8. A method according to claim 2 wherein said sample comprises protein.

9. A method according to claim 2 wherein said sample comprises nucleic acid.

10. The method of claim 1, further comprising determining an average intensity of a second bright bead type and positioning the registration grid such that the average intensity of the second bright bead type is maximal.

11. The method of claim 1, wherein the step of aligning the registration grid with the hybridization intensity image is performed prior to positioning the registration grid.

* * * * *